(12) United States Patent
Kyusojin et al.

(10) Patent No.: US 9,398,233 B2
(45) Date of Patent: Jul. 19, 2016

(54) PROCESSING APPARATUS, SYSTEM, METHOD AND PROGRAM FOR PROCESSING INFORMATION TO BE SHARED

(75) Inventors: Hiroshi Kyusojin, Tokyo (JP); Yoichi Mizutani, Saitama (JP); Yutaka Hasegawa, Kanagawa (JP); Masahiro Takahashi, Kanagawa (JP)

(73) Assignee: Sony Corporation, Tokyo (JP)

( * ) Notice: Subject to any disclaimer, the term of this patent is extended or adjusted under 35 U.S.C. 154(b) by 159 days.

(21) Appl. No.: 13/880,267

(22) PCT Filed: Jul. 10, 2012

(86) PCT No.: PCT/JP2012/004448
§ 371 (c)(1),
(2), (4) Date: Apr. 18, 2013

(87) PCT Pub. No.: WO2013/027323
PCT Pub. Date: Feb. 28, 2013

(65) Prior Publication Data
US 2013/0208078 A1 Aug. 15, 2013

(30) Foreign Application Priority Data
Aug. 22, 2011 (JP) .................................. 2011-180438

(51) Int. Cl.
*G06K 9/00* (2006.01)
*H04N 5/265* (2006.01)
(Continued)

(52) U.S. Cl.
CPC .............. *H04N 5/265* (2013.01); *G06F 19/321* (2013.01); *G06F 19/3425* (2013.01); *H04M 3/567* (2013.01); *H04N 7/15* (2013.01); *H04L 12/1827* (2013.01)

(58) Field of Classification Search
None
See application file for complete search history.

(56) References Cited

U.S. PATENT DOCUMENTS 5,519,436 A * 5/1996 Munson ............... H04N 19/507
348/14.13
5,968,120 A * 10/1999 Guedalia ....................... 709/219
(Continued)

FOREIGN PATENT DOCUMENTS

CN 1422405 A 6/2003
JP 10-171967 6/1998
(Continued)

OTHER PUBLICATIONS

Chinese Office Action issued Mar. 11, 2014 for corresponding Chinese Appln. No. 201280003348.5.
(Continued)

*Primary Examiner* — Utpal Shah
*Assistant Examiner* — Samah Beg
(74) *Attorney, Agent, or Firm* — K&L Gates LLP

(57) ABSTRACT

An information processing apparatus, an information processing system, and a method of processing information are provided. In one embodiment, the information processing apparatus includes a processor, and a memory device storing instructions. When executed by the processor, the instructions cause the processor to receive, from a first information processing apparatus, area specifying information and location information, the area specifying information specifying a display area in an image, the display area including a plurality of partial images, the location information indicating at least one location of the plurality of partial images. The instructions further cause the processor to transmit, to a second information processing apparatus, the area specifying information and the location information.

32 Claims, 18 Drawing Sheets

(51) Int. Cl.
*H04N 7/15* (2006.01)
*H04M 3/56* (2006.01)
*G06F 19/00* (2011.01)
*H04L 12/18* (2006.01)

(56) References Cited

U.S. PATENT DOCUMENTS

| | | | |
|---|---|---|---|
| 6,182,127 B1 | 1/2001 | Cronin, III et al. | |
| 6,396,941 B1* | 5/2002 | Bacus et al. | 382/128 |
| 6,597,392 B1* | 7/2003 | Jenkins et al. | 348/207.1 |
| 7,542,596 B2 | 6/2009 | Bacus | |
| 7,581,186 B2* | 8/2009 | Dowdy et al. | 715/727 |
| 7,979,055 B2 | 7/2011 | Watanabe et al. | |
| 2003/0200316 A1* | 10/2003 | Isozaki et al. | 709/225 |
| 2004/0066968 A1* | 4/2004 | Glickman | H04N 1/646 382/166 |
| 2004/0117445 A9 | 6/2004 | Lee et al. | |
| 2004/0141637 A1 | 7/2004 | Bacus et al. | |
| 2005/0034079 A1* | 2/2005 | Gunasekar | G06F 17/289 715/753 |
| 2006/0112069 A1* | 5/2006 | Gentles et al. | 707/1 |
| 2006/0129547 A1* | 6/2006 | Yamamoto et al. | 707/5 |
| 2006/0244867 A1* | 11/2006 | Saitou et al. | 348/699 |
| 2008/0306964 A1 | 12/2008 | Molnar et al. | |
| 2009/0179982 A1* | 7/2009 | Yanagisawa et al. | 348/14.1 |
| 2011/0128366 A1* | 6/2011 | Yoshioka et al. | 348/79 |
| 2011/0129135 A1* | 6/2011 | Mizutani et al. | 382/128 |
| 2011/0202848 A1* | 8/2011 | Ismalon | 715/738 |
| 2011/0254764 A1* | 10/2011 | Kimoto et al. | 345/157 |
| 2011/0282686 A1* | 11/2011 | Venon et al. | 705/3 |
| 2012/0011568 A1* | 1/2012 | Tahan | 726/4 |
| 2012/0036228 A1* | 2/2012 | Ichinose | H04N 1/00204 709/219 |
| 2013/0093781 A1* | 4/2013 | Suzuki et al. | 345/581 |
| 2013/0111387 A1* | 5/2013 | Li et al. | 715/771 |
| 2013/0304751 A1* | 11/2013 | Yoshioka et al. | 707/751 |
| 2013/0332857 A1* | 12/2013 | Kim | H04L 65/403 715/753 |
| 2014/0074913 A1* | 3/2014 | Claydon | H04L 67/1095 709/203 |

FOREIGN PATENT DOCUMENTS

| | | |
|---|---|---|
| JP | 10-301830 | 11/1998 |
| JP | 10-304330 | 11/1998 |
| JP | 2000-276120 | 10/2000 |
| JP | 2002-117415 | 4/2002 |
| JP | 2003-016021 | 1/2003 |
| JP | 2003-085070 | 3/2003 |
| JP | 2003-115873 | 4/2003 |
| JP | 3795772 | 7/2006 |
| JP | 2006-323448 | 11/2006 |
| JP | 2010-119142 | 5/2010 |
| JP | 2011-117991 | 6/2011 |
| JP | 2011-133849 | 7/2011 |
| JP | 2011-150400 | 8/2011 |

OTHER PUBLICATIONS

Tian et al., "A Novel Strategy to Access High Resolution DICOM Medical Images Based on JPEG2000 Interactive Protocol", Proc. of SPIE, 2008, vol. 6919 (12 pages).

European Search Report for Application No. 12825637.7 dated Jun. 9, 2015.

Japanese Office Action mailed Jun. 16, 2015 for Application No. 2011-180438.

Tuominen et al., Journal of Digital Imaging; vol. 23, No. 4 Aug. 2010: pp. 454-462; Linking Whole-Slide Microscope Images with DICOM by Using JPEG2000 Interactive Protocol.

* cited by examiner

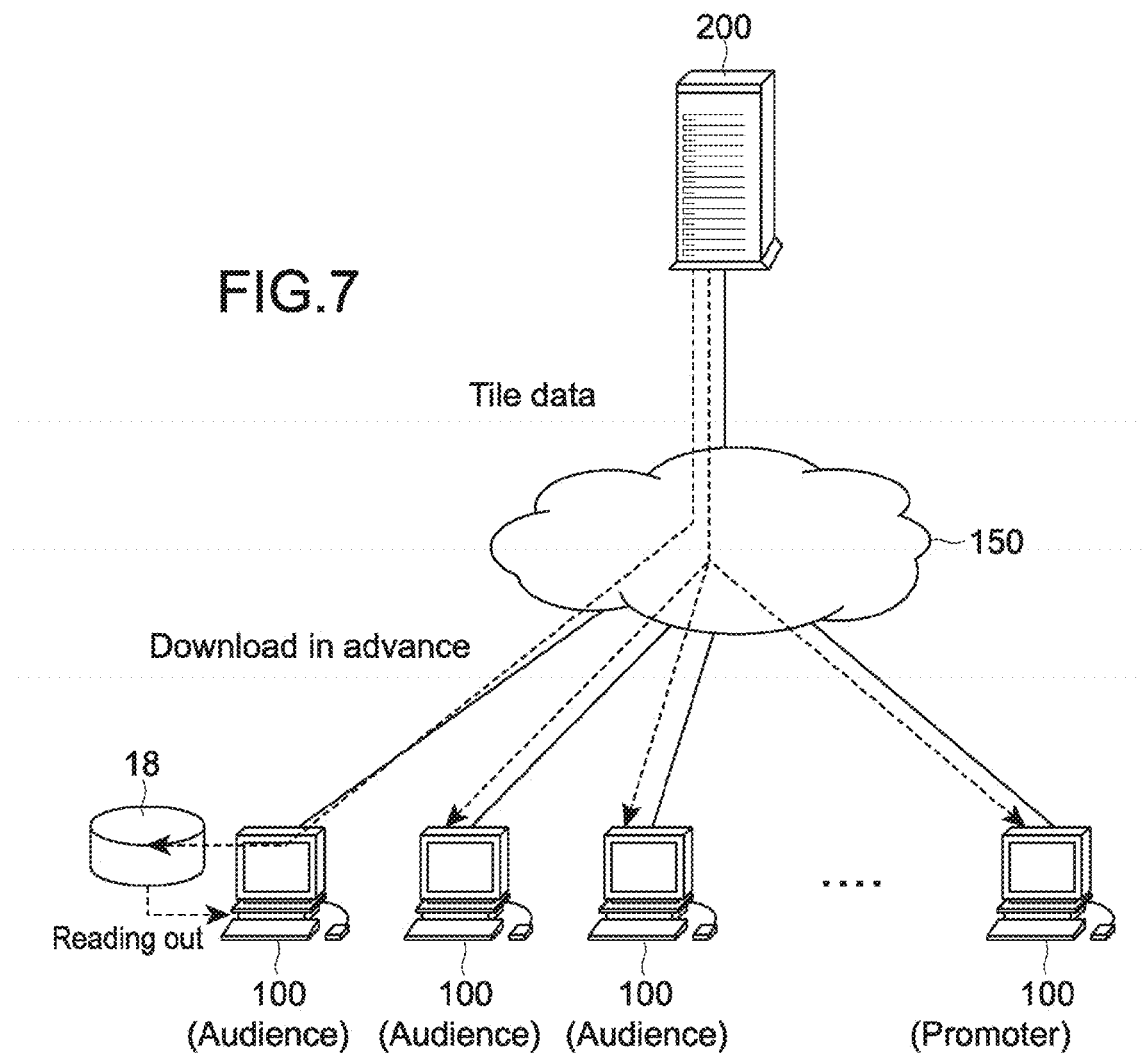
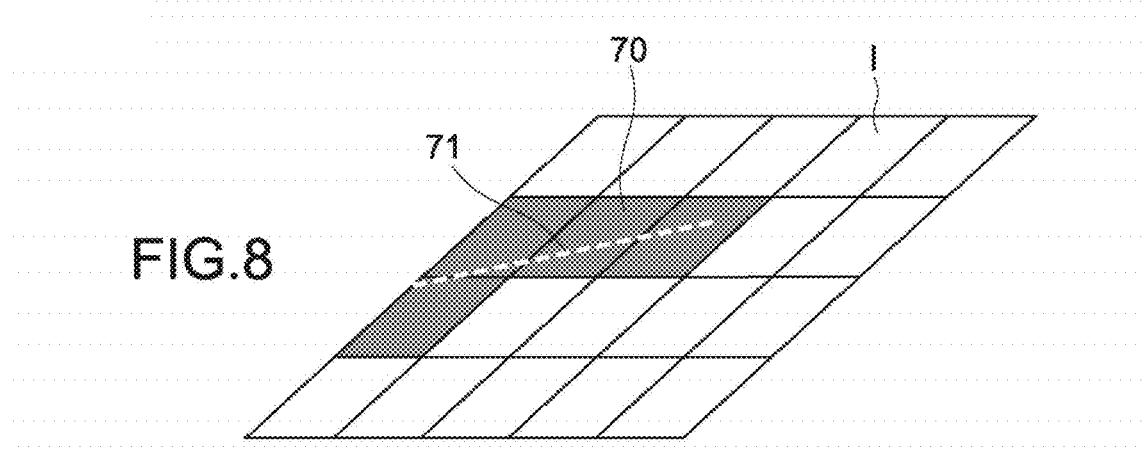

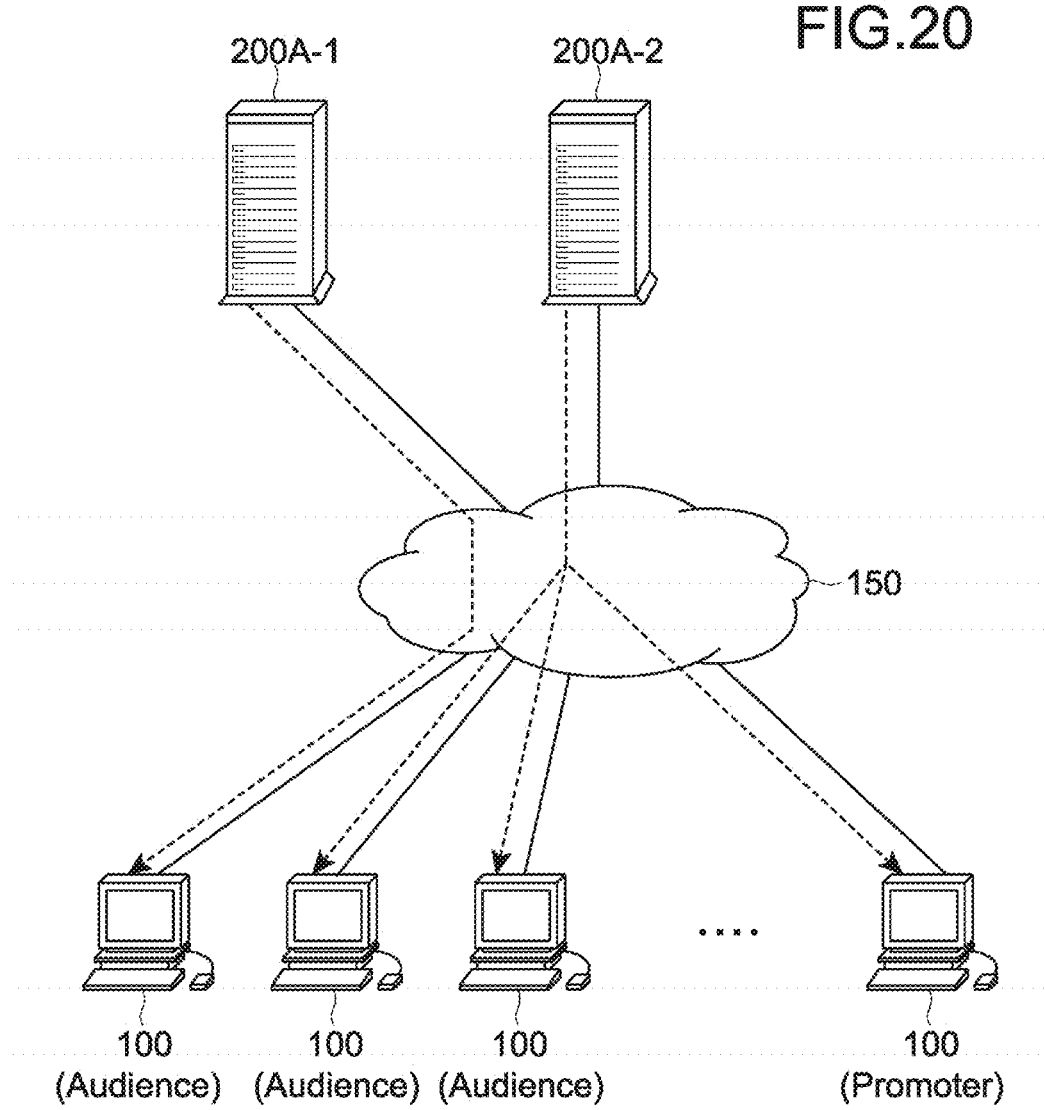

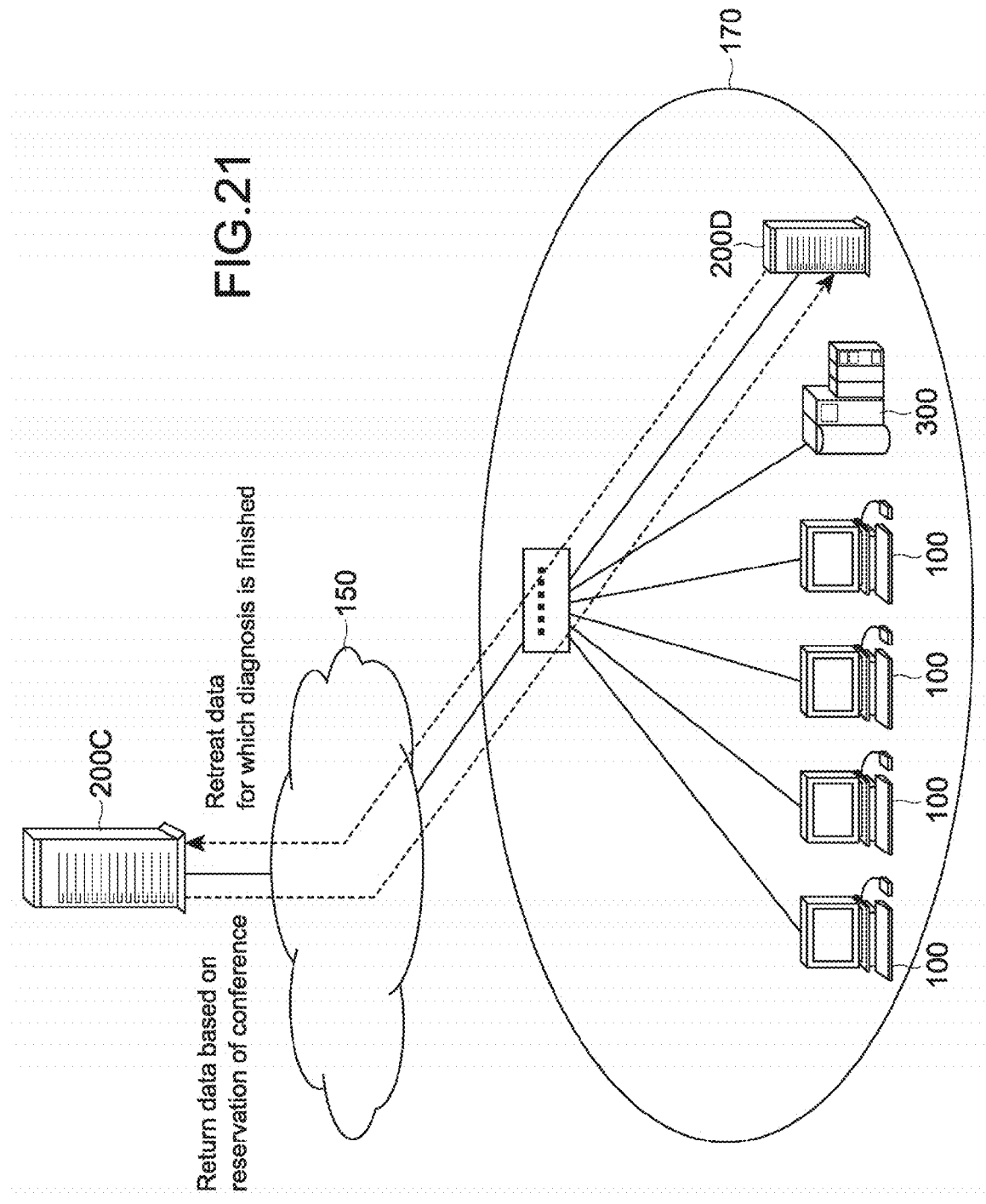

PROCESSING APPARATUS, SYSTEM, METHOD AND PROGRAM FOR PROCESSING INFORMATION TO BE SHARED

CROSS REFERENCES TO RELATED APPLICATIONS

The present application is a national stage of International Application No. PCT/JP2012/004448 filed on Oct. 7, 2012 and claims priority to Japanese Patent Application No. 2011-180438 filed on Aug. 22, 2011, the disclosure of which is incorporated herein by reference.

BACKGROUND

The present technology relates to an information processing apparatus which may have a pathology image in common with another information processing apparatus to make a user observe the image, an information processing system having the information processing apparatus, a method of processing information in the information processing apparatus, and a program for the information processing apparatus.

In the past, to support a teleconference among a plurality of users, a system (e.g., a television conference system) in which terminals of the users have a screen in common with one another as a common information resource has been known.

For example, in Patent Literature (PTL) 1 described later, an information communication service system, in which a conference is expedited while each of user terminals takes out contents registered in advance if necessary, is disclosed. In this system, a server receives videos and voices transmitted from a plurality of terminals in real time, synthesizes these ones, and delivers the synthesized ones to the terminals.

Further, in PTL 2 and PTL 3 described later, a content distributing system, in which contents are copied and dispersed to a plurality of servers to be stored, is described.

Moreover, PTL 4 described later discloses that a reproduction apparatus downloads in advance contents, of which the date and time to be provided for viewers is predetermined, from a server in a ciphered state, receives a key from the server at a viewable date and time, and deciphers the contents with the key to reproduce the contents.

Furthermore, in the field of pathological diagnosis, terminals of a plurality of users (e.g., doctors) have an image for pathological diagnosis in common with one another, and hold a teleconference to make a diagnosis while transmitting opinions among user's terminals. Therefore, the diagnosis is efficiently made.

In relation to this, in PTL 5 described later, a server and client system is disclosed. In this system, a server delivers a plurality of tile images composing a pathology image to clients, and each client synthesizes the pathology image from the tile images and views the pathology image.

CITATION LIST

Patent Literature

[PTL 1]
Japanese Patent No. 3795772
[PTL 2]
Japanese Patent Application Laid-open No. 2003-115873
[PTL 3]
Japanese Patent Application Laid-open No. 2003-085070
[PTL 4]
Japanese Patent Application Laid-open No. 2010-119142
[PTL 5]
U.S. Pat. No. 7,542,596

SUMMARY

However, in the case of constructing a common system of a pathology image, as described in PTL 1, in a tree type system for concentrating delivered data into a single point, because it is substantially required to gather data of a pathology image, photographed in each of terminals (hospitals), to a server of a cloud computing, it is time-consuming to upload the data. Further, when contents are concentrated into a single point, the contents act as a bottle neck, and scalability in simultaneously holding a plurality of conferences or the like may not be exhibited.

In a common system of normal contents, the problem in scalability may be solved by the technique described in each of PTL 2 and PTL 3. However, because data of a pathology image having a very high resolution have a large volume, it is time-consuming, in the same manner as in the uploading, to copy the data among a plurality of servers.

Further, in the technique described in PTL 4, the load on the server is decreased with the reduction of data communication performed during the conference. However, when the communication using the pathology image data is performed, it is very time-consuming to download the data in advance. Moreover, because only a slight portion of very huge volume of pathology image data is used for the pathological diagnosis, most of the downloaded data are not used. Therefore, efficiency in the download in advance is very low in view of effective use of a network band.

In view of the circumstances as described above, it is desirable to provide an information processing apparatus, an information processing system, and a method of processing information that are capable of shortening the time, taken to prepare the holding of a teleconference in which data of a pathology image are possessed in common, and expediting the teleconference efficiently and smoothly.

An information processing apparatus according to an embodiment of the present technology includes a processor, a display device, and a memory device storing instructions. When executed by the processor, the instructions cause the processor to: (a) in response to an operation input, determine area specifying information and location information, the area specifying information specifying a display area in an image, the display area including a plurality of partial images, the location information indicating at least one location of the plurality of partial images, (b) transmit the area specifying information and the location information to a first information processing apparatus, the first information processing apparatus being configured to, in response to receiving the area specifying information and the location information, transmit the area specifying information and the location information to a second information processing apparatus, (c) transmit a request for the plurality of partial images to the at least one location indicated by the location information, (d) receive the plurality of partial images from the at least one location, and (e) display the received plurality of partial images.

Therefore, because the information processing apparatus may receive each of the partial images of the pathology image from an arbitrary location being the same or different from locations of the other partial images, as compared with the case where the locations are concentrated into one point, the time required to prepare a teleconference using the pathology image with another information processing apparatus may be shortened. Further, because the information processing apparatus is not required to determine the display area in the pathology image, the teleconference using the pathology image may be expedited efficiently and smoothly by receiving the partial image according to the area specifying information and by displaying the partial image.

The information processing apparatus may further have storage. In this case, the processor may be configured to determine whether or not the partial images included in the display area are stored in the storage, and to be capable of controlling the display, when the partial images are stored in the storage, to display the partial images without transmitting the request information to the location.

Therefore, when the partial images are stored in the storage, it is not required that the information processing apparatus access the location. Accordingly, the traffic on the network may be reduced, and the teleconference using the pathology image may be further efficiently expedited.

The processor may be configured to be capable of controlling the information processing apparatus to receive, in advance, image specifying information, temporary location information, and diagnosis record information from the other information processing apparatus before receiving the area specifying information and the location information, the image specifying information specifying a pathology image that is capable of being used in a teleconference held with the other information processing apparatus, the temporary location information indicating a location of the specified pathology image at this time, the diagnosis record information indicating a past diagnosis record of the specified pathology image, and to receive a partial image, associated with the received diagnosis record information, among a plurality of partial images composing the pathology image specified by the received image specifying information, from the location indicated by the temporary location information. The processor may be configured to be capable of controlling the storage to store the received partial image.

Therefore, the information processing apparatus may download in advance a specific partial image, which may be used in the teleconference at a high probability, to store the specific partial image in the storage. Accordingly, the traffic during the teleconference may be reduced, and the teleconference using the pathology image may be efficiently expedited.

The processor may be configured to be capable of controlling the information processing apparatus to receive display record information, indicating one of a past display area and a display position in the specified pathology image, as the diagnosis record information. Therefore, the information processing apparatus may further efficiently expedite the teleconference using the pathology image by downloading in advance a partial image which may be displayed in the teleconference at a high probability in the same manner as in the past.

The processor may be configured to be capable of controlling the information processing apparatus to receive annotation information, affixed to a predetermined position in the specified pathology image, as the diagnosis record information.

Therefore, the information processing apparatus may further efficiently expedite the teleconference by downloading in advance the partial image to which annotation information is affixed and which may attract attention in the teleconference at a high probability in the same manner as in the past.

The pathology image may exist for each of a plurality of slices, which are taken out from one biological tissue and are stained with different colors, respectively, to form a plurality of pathology images. In this case, the processor may be configured to be capable of controlling the information processing apparatus to receive a partial image existing at a predetermined position, to which the annotation information is affixed, in a first pathology image of a slice stained with a first color, and to receive a partial image existing at the position same as the predetermined position in a second pathology image of a slice stained with a second color.

Therefore, the information processing apparatus may download in advance not only the partial image of the first pathology image, to which the annotation information is affixed, but also the partial image of the second pathology image which is taken from the biological tissue in common with the first pathology image but is of a slice stained in a color differing from that in the first pathology image.

Images of a slice taken out from one biological tissue may be taken at a plurality of different resolutions, and the pathology image may exist for each of the plurality of resolutions to form a plurality of pathology images. In this case, the processor may be configured to be capable of controlling the information processing apparatus to receive a partial image existing at a predetermined position, to which the annotation information is affixed, in a first pathology image taken at a first resolution, and to receive a partial image existing at the position same as the predetermined position in a second pathology image taken at a second resolution.

Therefore, the information processing apparatus may download in advance not only the partial image of the first pathology image, to which the annotation information is affixed, but also the partial image of the second pathology image which is taken from the biological tissue in common with the first pathology image but of which the resolution differs from the resolution of the first pathology image.

The processor may be configured to be capable of controlling the information processing apparatus to receive the area specifying information from the other information processing apparatus via a first server apparatus. In this case, the location may indicate a second server apparatus different from the first server apparatus.

Therefore, the pathology image and the area specifying information are managed in different servers, respectively. Accordingly, it may be prevented that the concentration of the load on a specific server disturbs the expedition of the teleconference.

An information processing apparatus according to another embodiment includes a processor, and a memory device storing instructions. When executed by the processor, the instructions cause the processor to: (a) receive, from a first information processing apparatus, area specifying information and location information, the area specifying information specifying a display area in an image, the display area including a plurality of partial images, the location information indicating at least one location of the plurality of partial images; and (b) transmit, to a second information processing apparatus, the area specifying information and the location information.

According to another embodiment of the present technology, there is provided an information processing apparatus comprising: a processor, a display device, and a memory device storing instructions. When executed by the processor, the instructions cause the processor to: (a) receive area specifying information and location information from a first information processing apparatus, the area specifying information specifying a display area in an image, the display area including a plurality of partial images, the location information indicating at least one location of the plurality of partial images, (b) transmit a request for the plurality of partial images to the at least one location indicated by the location information, (c) receive the plurality of partial images from the at least one location, and (d) display the received plurality of partial images.

According to still another embodiment of the present technology, there is provided a method of operating an information processing apparatus. The method includes (a) causing a processor to execute instructions to receive, from a first information processing apparatus, area specifying information and location information, the area specifying information specifying a display area in an image, the display area including a plurality of partial images, the location information indicating at least one location of the plurality of partial images, and (b) causing the processor to execute instructions to transmit, to a second information processing apparatus, the area specifying information and the location information.

According to still another embodiment of the present technology, there is provided a system including a first, second, and third information processing apparatus. The first information processing apparatus is configured to, in response to an operation input, determine area specifying information and location information, the area specifying information specifying a display area in an image, the display area including a plurality of partial images, the location information indicating at least one location of the plurality of partial images. The second information processing apparatus is configured to receive the area specifying information and the location information from the first information processing apparatus. The third information processing apparatus is configured to: (a) receive the area specifying information and the location information from the second information processing apparatus, (b) transmit a request for the plurality of partial images to the at least one location indicated by the location information, (c) receive the plurality of partial images from the at least one location; and (d) display the received plurality of partial images.

As described above, according to the present technology, the time required to prepare the holding of a teleconference in which data of the pathology image are possessed in common may be shortened, and the teleconference may be expedited efficiently and smoothly.

Additional features and advantages are described herein, and will be apparent from the following Detailed Description and the figures.

BRIEF DESCRIPTION OF THE FIGURES

FIG. 7 is a block diagram showing the configuration of a teleconference system according to a second embodiment of the present technology.

FIG. 8 is a diagram showing the specification of tiles, to be downloaded in advance, on the basis of past operation record information in the system according to the second embodiment.

FIG. 20 is a block diagram showing the configuration of a teleconference system according to a sixth embodiment.

FIG. 21 is a block diagram showing the configuration of a teleconference system according to a seventh embodiment.

DETAILED DESCRIPTION

Hereinafter, embodiments according to the present technology will be described with reference to drawings.

First Embodiment

Initially, the first embodiment according to the present technology will be described.
[Outline of System]

Figure 1:
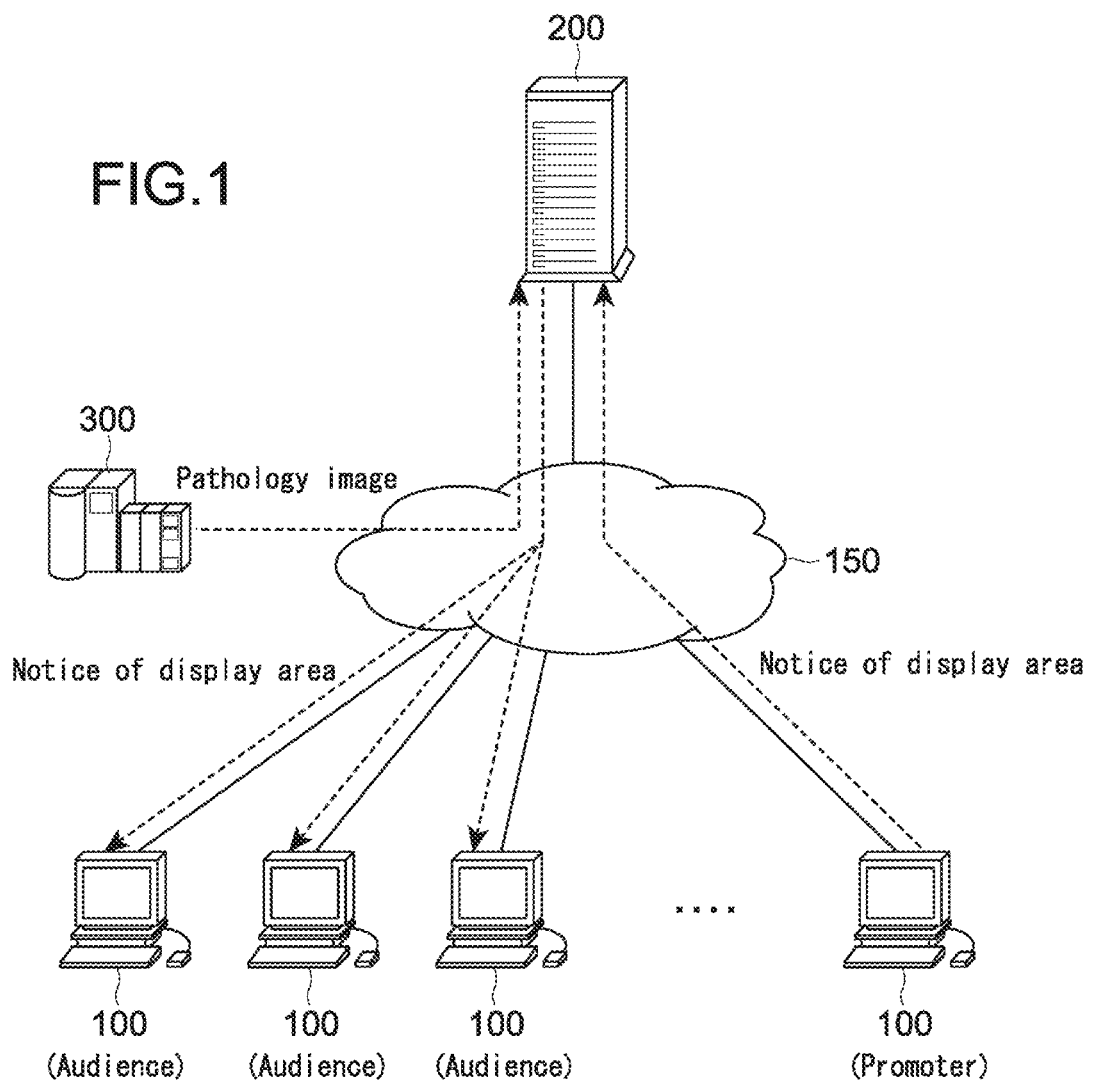
FIG. 1 is a block diagram showing the configuration of a teleconference system according to a first embodiment of the present technology.

FIG. 1 is a block diagram showing the configuration of a teleconference system using a pathology image according to the first embodiment. In this system, a diagnosis is efficiently made by holding a teleconference, while personal computers (PCs) of a plurality of users (e.g., doctors) have an image for pathological diagnosis (a pathology image) in common with one another, and by making a diagnosis while opinions are transmitted among the PCs.

As shown in this figure, this system has a server 200, a plurality of PCs 100, and a scanner 300. These may communicate with one another via the Internet 150.

Data of a pathology image taken by the scanner 300 are uploaded to the server 200 via the Internet 150 and are stored. As described later in detail, the pathology image is obtained by taking an image of a slice of a biological tissue or the like held in a glass slide. The pathology image data are not stored only in the server 200, but may be stored in any of the PCs 100.

In this system, one of the plurality of PCs 100 acts as the "chairman" of the teleconference, and the other ones act as "audiences". A pathology image specified by the PC 100 as the chairman is displayed on the PCs 100 as audiences.

As described later in detail, the PC 100 acting as the chairman transmits information (area specifying information), specifying a display area in the pathology image for a diagnosis in the teleconference, and information (URL; uniform resource locator), indicating locations of the pathology image data, to the server 200. The server 200 transmits the area specifying information and the URL to the PCs 100 acting as the audiences. That is, the PC 100 acting as the chairman transmits the area specifying information and the URL to the PCs 100 acting as the audiences via the server 200.

Each PC 100 acting as the audience receives an image (a partial image) of the pathology image existing in the area, specified by the area specifying information, from the URL and displays the partial image. Therefore, the PCs 100 have the pathology image in common with one another, and a pathological diagnosis may be made by the users of the PCs 100.

[Hardware Configuration of PC]

Figure 2:
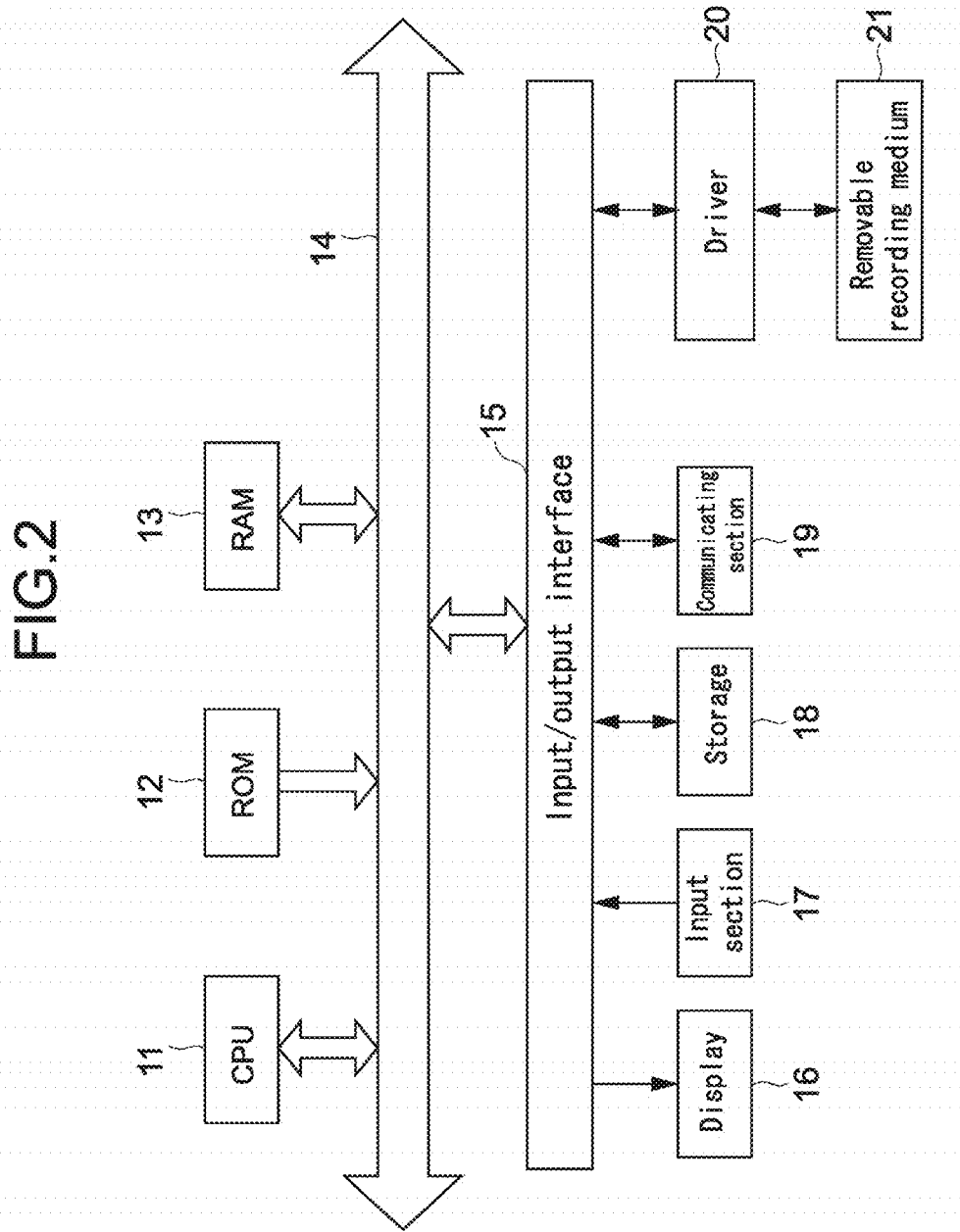
FIG. 2 is a block diagram showing the configuration of hardware of a PC in the system.

FIG. 2 is a block diagram showing the hardware configuration of one PC 100.

Each PC 100 has a central processing unit (CPU) 11, a read only memory (ROM) 12, a random access memory (RAM) 13, an input/output interface 15, and a bus 14 connecting these ones with one another.

The input/output interface 15 is connected with a display 16, an input section 17, storage 18, a communicating section 19, a driver 20, and the like.

The display 16 is, for example, a display device using liquid crystal, electro-luminescence (EL) or the like.

The input section 17 is, for example, a pointing device, a keyboard, a touch panel, a microphone, or another operating device. When the input section 17 includes a touch panel, the touch panel may be integrally formed with the display 16.

The storage 18 is a nonvolatile storage device, for example, being a hard disk drive (HDD), a flash memory, or another solid memory. In the storage 18, not only the pathology image data are stored, but also an application program, to be executed to receive and display the pathology image data in this system, is stored.

The driver 20 is, for example, a device capable of driving a removable recording medium 21 such as an optical recording medium, a floppy (registered trademark) disk, a magnetic recording tape, or a flash memory. In contrast, the storage 18 is often used as a device which is mounted in the PC 100 in advance and drives a non-removable recording medium.

The communicating section 19 is a modem, a router, or another communicating device which communicates with another device and may be connected to a local area network (LAN), a wide area network (WAN), or the like. The communicating section 19 may use any of wire communication and wireless communication. The communicating section 19 is often used while being formed independent of the PC 100.

The hardware configuration of the server 200 is also the same as the hardware configuration of the PC 100 and has blocks such as a control section, storage, and a communicating section being necessary to act as a computer.

Figure 3:
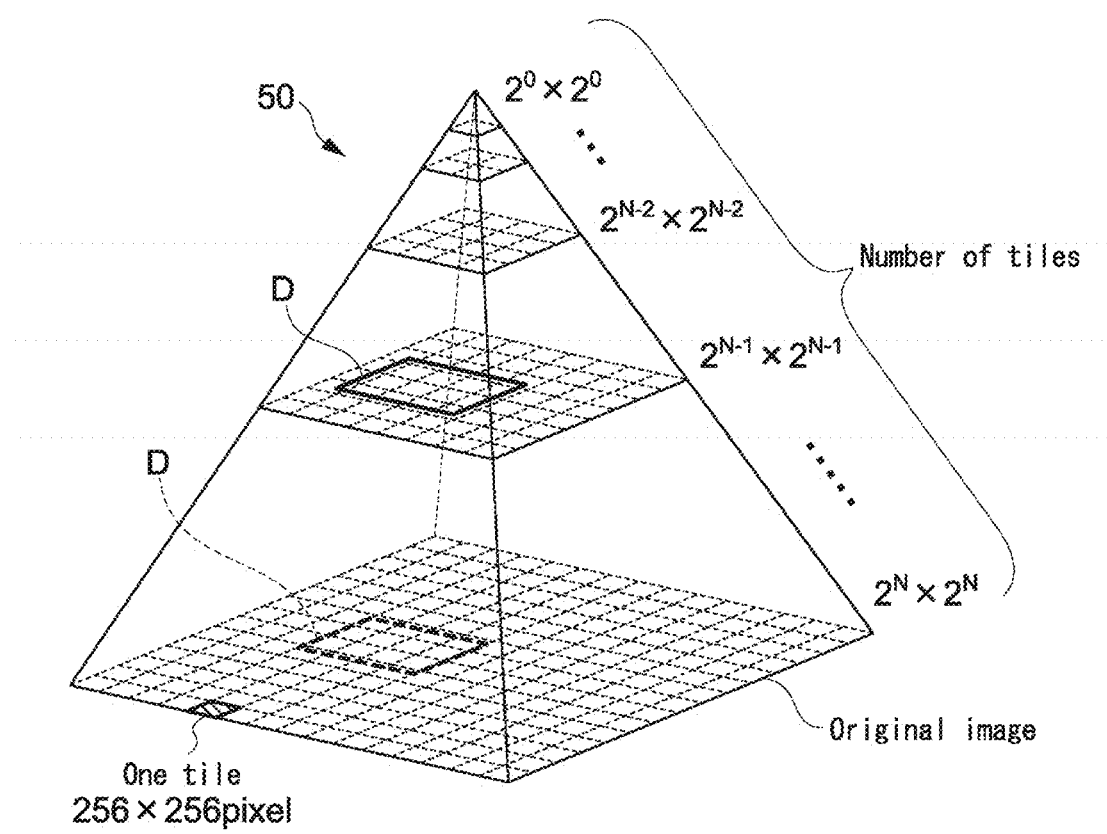
FIG. 3 is a diagram explaining a display principle of a pathology image treated in the system.

Next, a pathology image, which may be stored in the server 200 or the storage 18 of the PC 100, and a display principle of the image will be described. FIG. 3 is a diagram showing an image pyramid structure for explaining the display principle.

An image pyramid structure 50 according to this embodiment is an image group (a total image group) of which images are produced from a single pathology image, obtained from a single observation object 40 (see FIG. 4) by an optical microscope, at a plurality of different resolutions respectively. The image having the largest size is located in the lowest layer of the image pyramid structure 50, while the image having the smallest size is located in the highest layer. The resolution of the largest sized image is, for example, 50×50 kilopixels or 30×40 kilopixels. The resolution of the smallest sized images is, for example, 256×256 pixels or 256×512 pixels.

That is, when the same display 16 displays these images, for example, in 100% size (each of the images is displayed at the number of physical dots which is the same as the number of pixels in the image), the image having the largest size is displayed in the largest size, and the image having the smallest size is displayed in the smallest size. Here, in FIG. 3, the display area of the display 16 is indicated by D.

Figure 4:
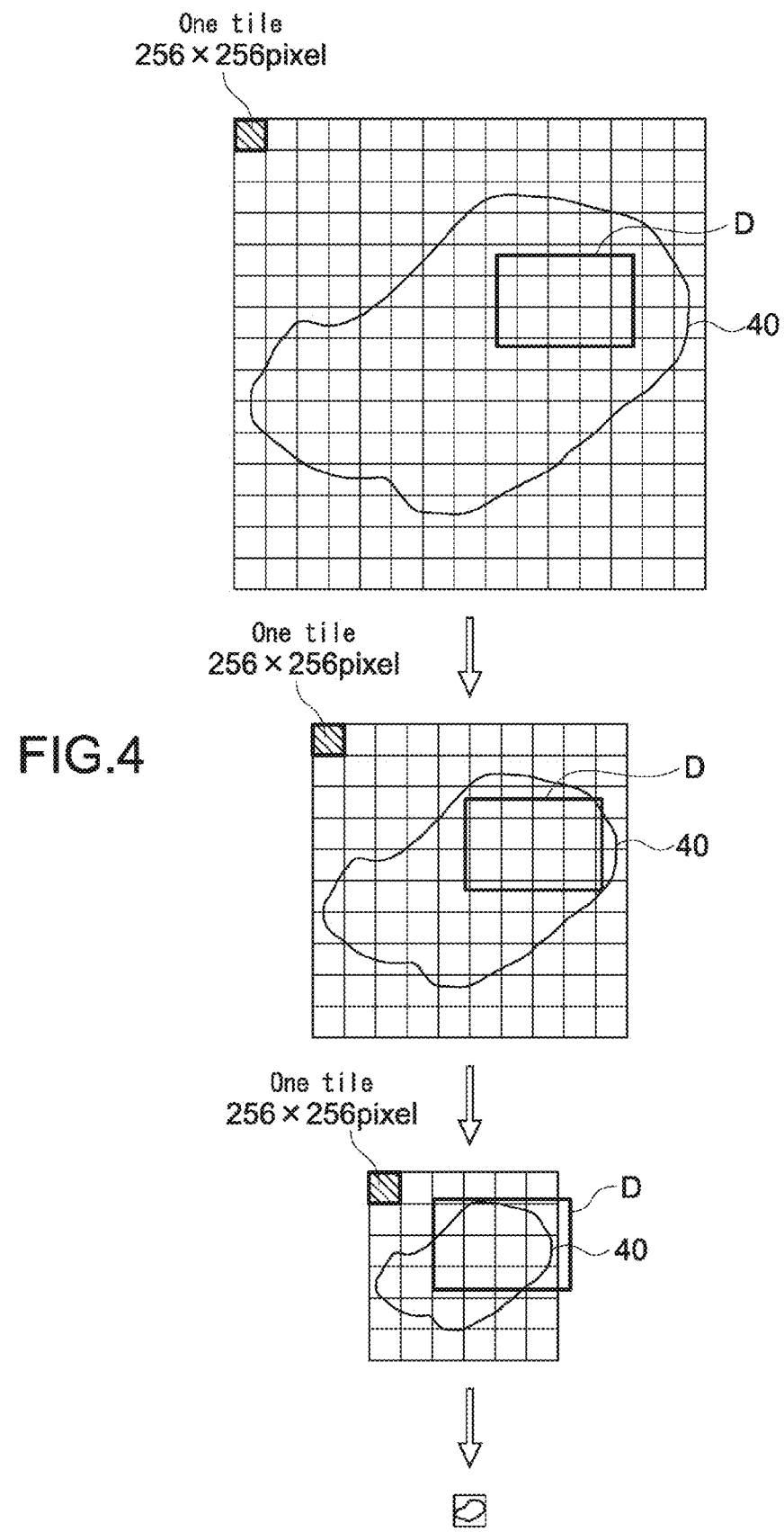
FIG. 4 is a diagram indicating the procedure in the case of producing an image group of the pathology image treated in the system.

FIG. 4 is a diagram for explaining the procedure in the case of producing the image group of the image pyramid structure 50.

Initially, a digital image of an original image (a huge image) obtained at a predetermined observation magnification by an optical microscope (not shown) is prepared. This original image is equivalent to the largest sized image being the lowest image of the image pyramid structure 50 shown in FIG. 3, and is an image having the highest resolution. Therefore, as the lowest image of the image pyramid structure 50, an image obtained by observing at a comparatively high resolution by the optical microscope is used.

In the field of pathology, generally, a slice thinly cut off from a living internal organ, a biological tissue, a cell, or a part of any one of these is an observation object 40. Then, the observation object 40 held in a glass slide is read out by the scanner 300 having the function of an optical microscope, and an obtained digital image is stored in the scanner 300 or other storage.

As shown in FIG. 4, this scanner 300 or a generally-used computer (not shown) produces a plurality of images which respectively have resolutions lowered step by step from the largest sized image obtained as described above, and stores these images, for example, every "tile" (partial image) unit denoting a unit of a predetermined size. The size of one tile is, for example, 256×256 pixels. To each tile, identification information (an ID or a number) identifying the tile is added.

The image group produced as described above forms the image pyramid structure 50, and this image pyramid structure 50 is stored in the storage 18 of the PC 100 or storage of the server 200. Practically, the PC 100 or the server 200 may store the images having a plurality of different resolutions and pieces of information of the resolutions while the images are associated with the pieces of information respectively. The PC 100 may perform the production and storage of the image pyramid structure 50.

The total image group forming this image pyramid structure 50 may be produced by a known compression method, and may be, for example, produced by a known compression method for producing a thumbnail image.

When the user of each PC 100 views the pathology image stored in the storage 18 of the PC 100 not in a teleconference but in stand-alone, the PC 100 extracts a desired image from the image pyramid structure 50 in response to the operation of the user input from the input section 17 and displays this image on the display 16. In this case, the PC 100 displays an image of an arbitrary portion, selected by the user, from among images having an arbitrary resolution selected by the user. While the user changes the observation magnification, the user may obtain a feeling that the user actually observes the observation object 40. That is, in this case, the PC 100 acts as a virtual microscope, and a virtual observation magnification is practically equivalent to the resolution described above.

[Operation of System]

Next, an operation of the system configured as described above will be described. Hereinafter, an operation will be described while especially setting the CPU 11 of the PC 100 as a main operating subject, and the operation is performed in cooperation with other blocks of each device and software (application).

Figure 5:
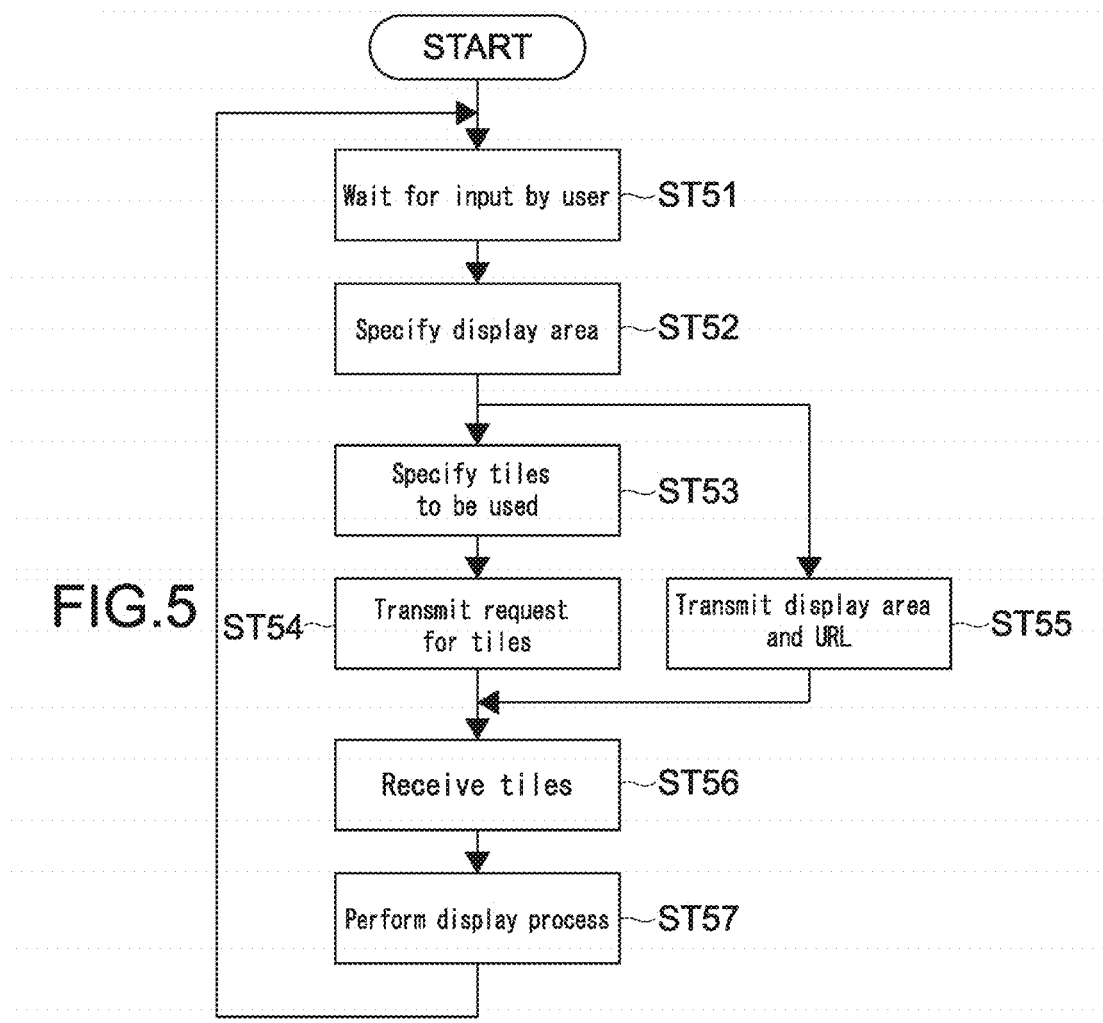
FIG. 5 is a flowchart showing the processing in a PC being the chairman when a pathology image is displayed in the system.
Figure 6:
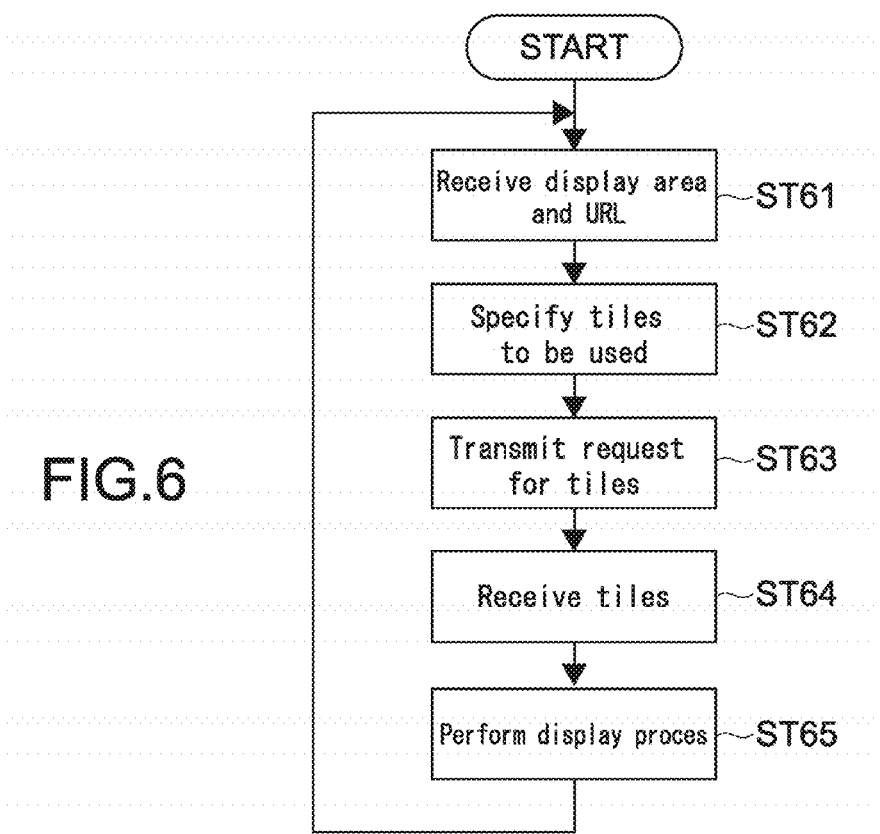
FIG. 6 is a flowchart showing the processing in a PC being an audience when a pathology image is displayed in the system.

FIG. 5 is a flowchart showing the processing in the PC 100 being the chairman when a pathology image is displayed according to this embodiment, while FIG. 6 is a flowchart showing the processing in the PC 100 being one audience in this case.

As shown in FIG. 5, the CPU 11 of the PC 100 being the chairman waits for an operation input of the user which specifies a display area in a specific pathology image (step 51) and specifies the display area when receiving this operation input (step 52).

Then, on the basis of the specified display area, the CPU 11 specifies tiles of the pathology image used for the display process, that is, tiles (partial images) of which all or a part is included in the display area (step 53).

Then, the CPU 11 transmits a request for data of the specified tiles to the server 200 (step 54). On the other hand, the CPU 11 transmits display area information indicating the display area and a URL of the specified tile data to the server 200 (step 55).

Then, the CPU 11 receives the tile data transmitted from the server 200 in response to the request (step 56) and displays the tile data on the display (step 57).

On the other hand, as shown in FIG. 6, the CPU 11 of the PC 100 being each audience receives the display area information and the URL transmitted from the PC 100 being the chairman via the server 200 (step 61).

Then, the CPU 11 specifies tiles of the pathology image required for the display process of the display area on the basis of the display area information (step 62).

Then, the CPU 11 transmits the request for the specified tiles to the server 200 on the basis of the received URL (step 63).

Then, the CPU 11 receives tiles transmitted in response to the request (step 64), and displays the tiles on the display 16 (step 65).

Second Embodiment

Next, the second embodiment according to the present technology will be described.

FIG. 7 is a block diagram showing the configuration of a teleconference system according to this embodiment.

In the first embodiment described above, the pathology image is stored in the server 200, and is downloaded to the PC 100 on the day on which the teleconference is held. However, as shown in this figure, when the day fixed for the teleconference and a pathology image used in the teleconference are predetermined, the PC 100 may also download the pathology image to the storage 18 before the conference is held. This downloading may be performed in a tile unit without being performed in a unit of the whole pathology image.

In the above-described download in a tile unit in advance, each tile being used in the teleconference at a high probability may be downloaded. The tiles being used at a high probability are, for example, the tiles used for a pathological diagnosis in the past. The tiles used for a past pathological diagnosis are, for example, specified according to a following criterion.

That is, the PC 100 specifies tiles used for a past diagnosis on the basis of a display operation record indicating that at which magnification (resolution) a doctor making a diagnosis in the past viewed a pathology image and how the doctor moved coordinates or a display area.

Figure 9:
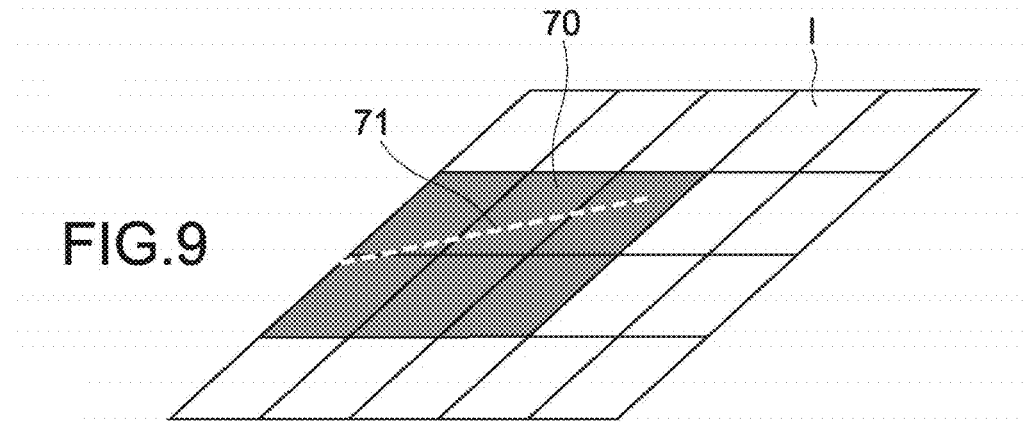
FIG. 9 is a diagram showing the specification of tiles, to be downloaded in advance, on the basis of past operation record information in the system according to the second embodiment.
Figure 10:
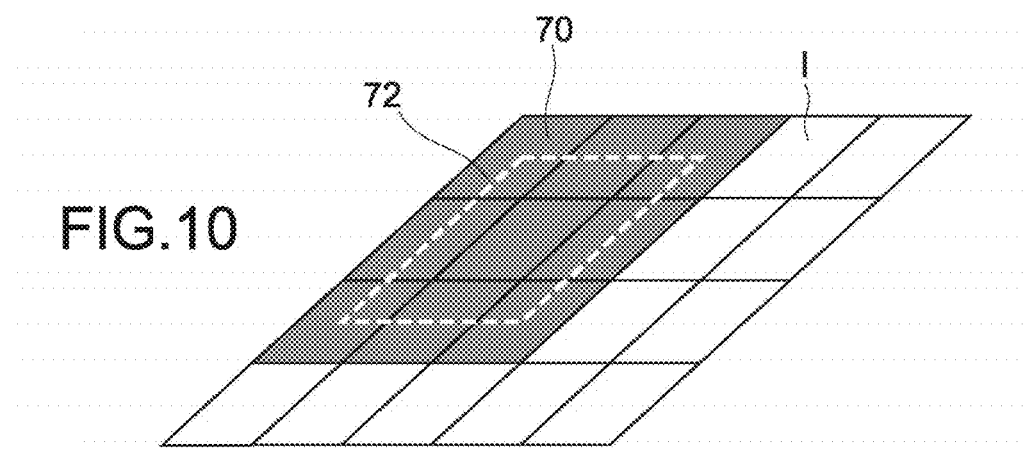
FIG. 10 is a diagram showing the specification of tiles, to be downloaded in advance, on the basis of past operation record information in the system according to the second embodiment.

FIG. 8, FIG. 9, and FIG. 10 are diagrams showing examples of tiles specified on the basis of this operation record information.

As shown in FIG. 8, when the operation record of a pathology image I is indicated as a coordinate moving path 71 being a line, tiles 70 (tiles to which the line belongs) on which the line goes across are specified. Further, when the operation record is indicated by a point (specific coordinates), a tile including this point is specified.

Further, as shown in FIG. 9, even in the same case as that in FIG. 8, tiles 70 being formed in a rectangle and including the line may be specified.

Further, as shown in FIG. 10, when the operation record of the pathology image I is indicated as a display area 72 of a rectangle, each tile 70 of which all or a part is included in this rectangle is specified.

Furthermore, when some diagnosis annotation is affixed to a pathology image by a doctor in a past diagnosis, the PC 100 specifies a tile to which this annotation is affixed. The annotation denotes information which is, for example, formed in a style of a symbol, a diagram, a text, a voice, an image, a link (e.g., URL), or the like on the basis of user's input on the PC displaying the pathology image.

Figure 11:
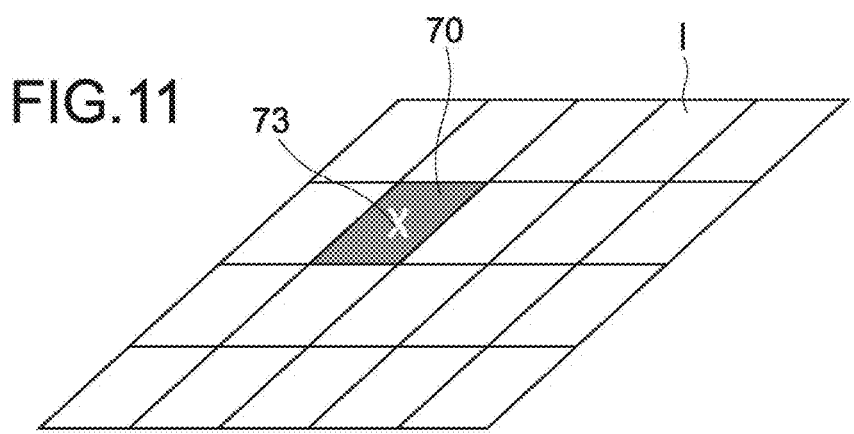
FIG. 11 is a diagram showing the specification of a tile, to be downloaded in advance, according to past annotation information in the system according to the second embodiment.

For example, as shown in FIG. 11, a tile 70, to which an annotation 73 indicated by a symbol X is affixed, among tiles composing the pathology image I is specified. When the annotation indicated by a line, a rectangle, or a circle is affixed, in the same manner as in FIG. 8 to FIG. 10, tiles on which the line goes across or tiles included in the rectangle or the circle are specified.

Figure 12:
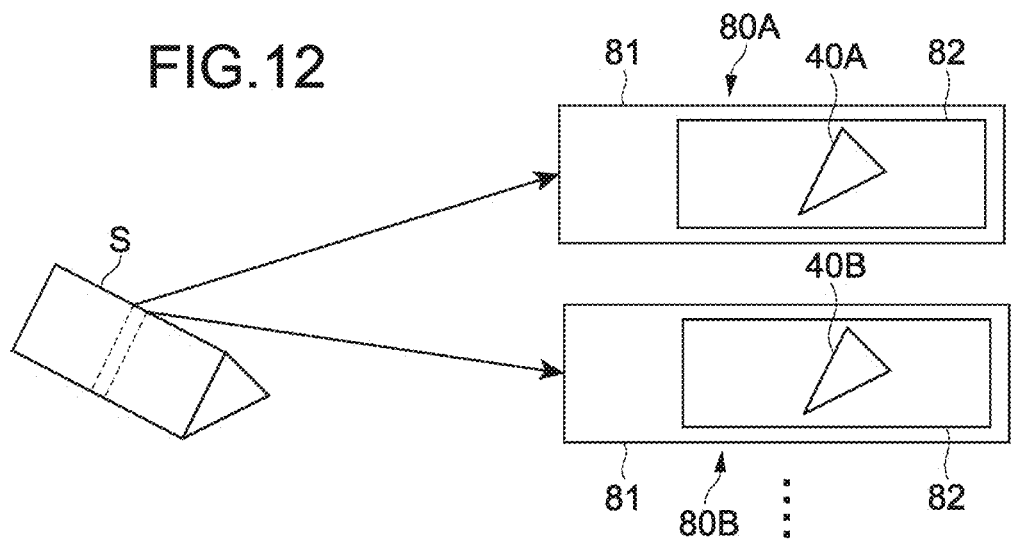
FIG. 12 is a diagram showing the production of a pathology slide from a plurality of slices of a biological tissue.

FIG. 12 is a diagram showing the preparation of slides (pathology slides) in which slices are held to be photographed for pathology images.

As shown in this figure, a pathology slide 80 is prepared by cutting off the observation object (a slice) 40 at the thickness of two to three micrometers from a pathology piece (a biological tissue) S taking out by a surgery or the like, mounting the slice 40 on a slide glass 81, and covering the slice 40 with a cover glass 82.

Accordingly, slices successively cutting off have approximately the same tissue shape and the same medical feature of cell and the like. That is, as shown in this figure, diagnosis information affixed to a pathology slide 80A of a slice 40A is also useful for an adjacent pathology slide 80B of a slice 40B.

There is the case where the different slices 40A and 40B are stained with different colors to perform different inspections respectively. Accordingly, when a plurality of pathology images relating to the successive slices stained with different colors exist, the PC 100 specifies a tile of one pathology image to which an annotation is affixed, and specifies a tile of another pathology image existing at the same coordinates as those of the position at which the annotation is affixed.

Further, as described above, the user may see one pathology image while changing the observation magnification (the resolution). Accordingly, when an annotation is affixed to a certain pathology image, this annotation is also useful information for another pathology image of the same observation object of which the magnification (the resolution) differs from that of the certain pathology image. Accordingly, when an annotation is affixed to a certain pathology image, the PC 100 specifies a tile of the certain pathology image to which the annotation is affixed, and also specifies a tile, which includes the same coordinates as coordinates at which the annotation is affixed, in another pathology image of the same observation object having a different resolution.

Figure 13:
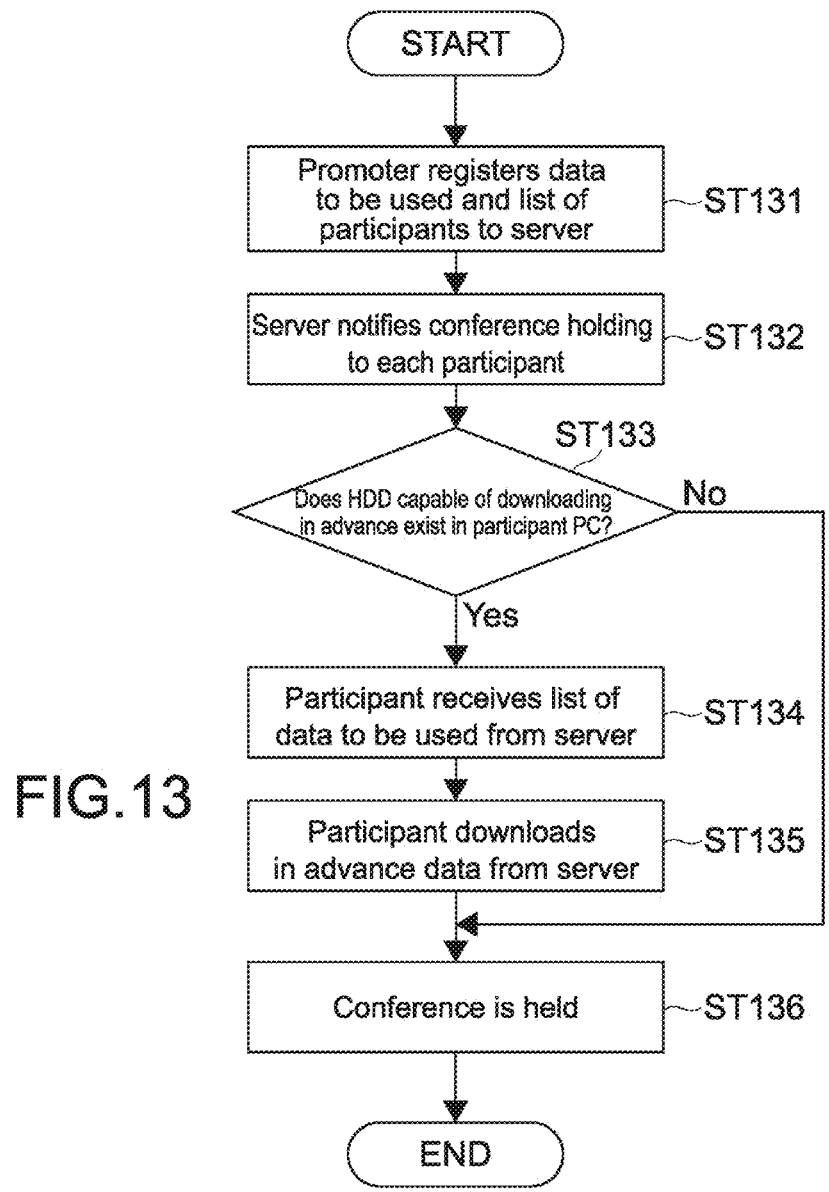
FIG. 13 is a flowchart showing one example of the processing in a PC and a server when a pathology image is downloaded in advance in the system according to the second embodiment.

FIG. 13 is a flowchart showing the processing in the PC 100 and the server 200 in the download of a pathology image in advance.

As shown in this figure, initially, pathology image data to be used for a teleconference and a list of participants of the teleconference are transmitted from the PC 100 of the promoter of the teleconference to the server 200 and are registered (step 131). This process is, for example, performed by selecting a desired pathology image and users from data of all pathology images and a list of all users existing in the server 200.

Then, the server 200 transmits a notice of a conference holding to the PC 100 of each participant (step 132).

Then, the PC 100 of each participant determines whether or not the storage 18 such as a HDD having a capacity capable of downloading a pathology image in advance exists in the PC 100 (step S133).

When a HDD capable of downloading exists (YES), the PC 100 of the participant receives a list of pathology image data to be used in the teleconference from the server 200 (step 134). In this case, past diagnosis record information relating to these pathology image data and the URL of the pathology image data (tiles) at this time are also received.

Then, the PC 100 specifies tiles according to the criterion described above on the basis of the received list of pathology image data and the received diagnosis record information, and downloads the specified tiles from the server 200 (step 135).

Then, when the start time of the teleconference comes, the PC 100 of the participant may participate in the conference by being connected to the server 200 (step 136).

In the example shown in FIG. 13, at the time when the promoter registers the pathology image data to the server 200, the list of data to be used in the conference is determined. However, practically, in the period of time from the time when a request for the holding of a conference is transmitted to the time when the conference is held, there is the case where the list is updated by deleting unnecessary data by the promoter, or by adding, by another participant, data that this participant wishes to use.

Figure 14:
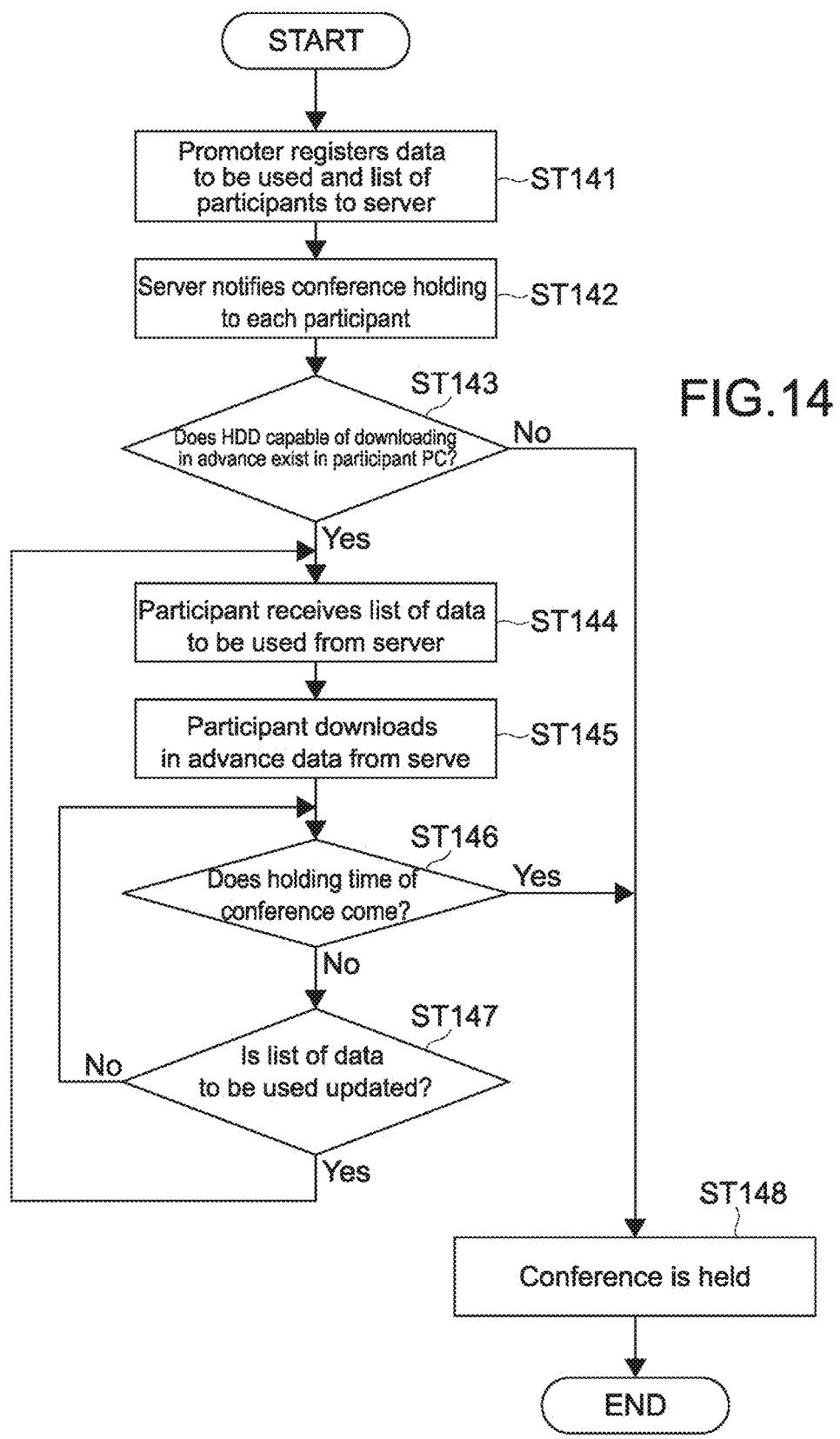
FIG. 14 is a flowchart showing another example of the processing in a PC and a server when a pathology image is downloaded in advance in the system according to the second embodiment.

Therefore, as shown in the flowchart of FIG. 14, there is the idea that the list is maintained to an updated one by polling the list.

That is, as shown in this figure, at step 141 to step 145, after the PC 100 performs the same processes as those at step 131 to step 135 of FIG. 13, the PC 100 determines whether or not the start time of the teleconference comes (step 146).

Then, when the start time of the teleconference does not yet come (NO), the PC 100 accesses the server 200 and determines whether or not the list of pathology image data to be used has been updated (step 147).

When the list has been updated (YES), the PC 100 receives a new list from the server 200 and repeats the processes performed at step 144 and steps following step 144.

Here, in place of the processes at step 146 and step 147, the PC 100 may receive a new list in response to a notice that indicates the update of the list and is sent from the server 200 to the PC 100 of each participant.

Further, the destination to which tiles are downloaded in advance is not limited to the storage 18 of the PC 100. For example, the downloading to a neighboring storage device connected with the PC 100 via a network is possible. When there are a plurality of servers 200, the downloading to the server 200 closest to the PC 100 is allowed.

Figure 15:
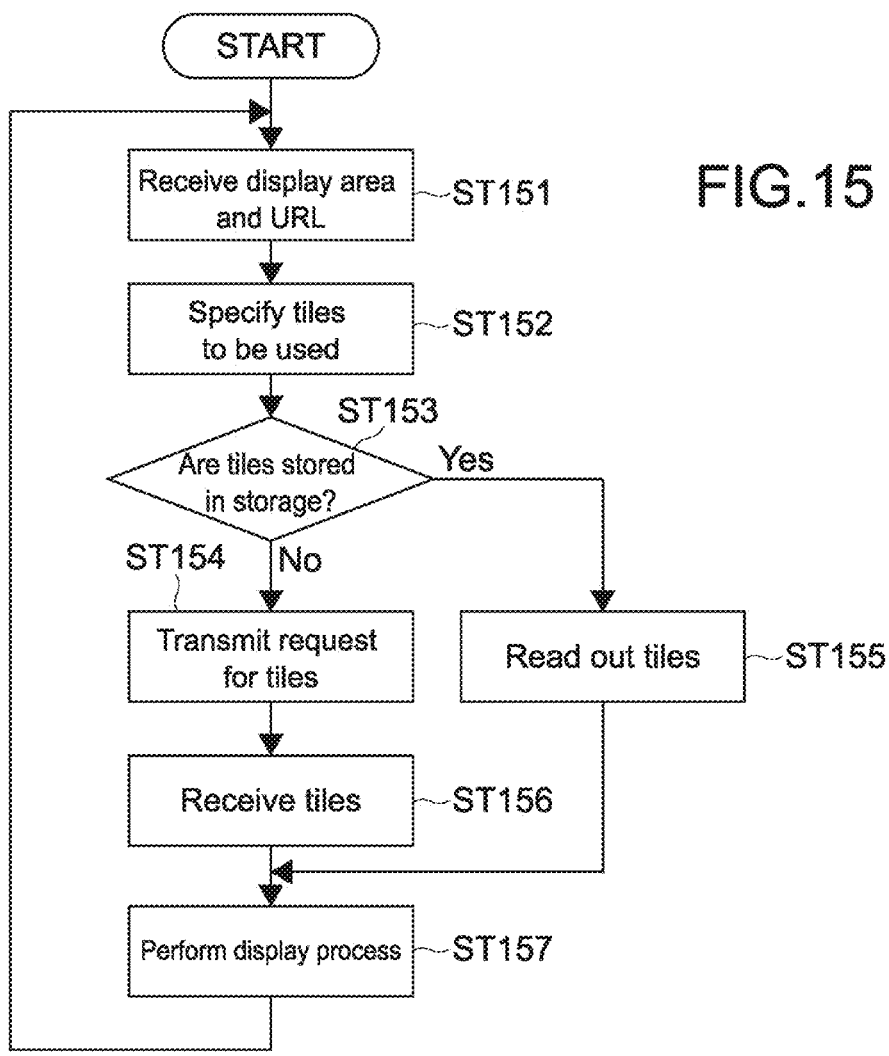
FIG. 15 is a flowchart showing the processing in a PC being an audience when a pathology image is displayed in the system.

FIG. 15 is a flowchart showing the processing in the PC 100 being an audience when a pathology image is displayed in the system according to this embodiment.

As shown in this figure, after the CPU 11 of the PC 100 performs the same processes as those at step 61 and step 62 shown in FIG. 6 according to the first embodiment (steps 151 and 152), the CPU 11 determines whether or not specified tiles are stored in the storage 18 (whether or not specified tiles have been downloaded in advance) (step 153).

When the tiles do not exist in the storage 18 (NO), the CPU 11 transmits a request for the tiles to the server 200 (step 154), and receives the tiles (step 156).

When the tiles are stored in the storage 18 (YES), the CPU 11 reads out the tiles from the storage 18 (step 155).

Then, the CPU 11 displays the tiles, received or read out, on the display 16 (step 157).

As described above, according to the download in advance, unnecessary communication on the date of the teleconference is reduced. Accordingly, the load on the server 200 expected when the number of PC 100 being audiences is increased may be reduced, and unnecessary packets transmitted through the network may be avoided.

Third Embodiment

Next, a third embodiment according to the present technology will be described.

Figure 16:
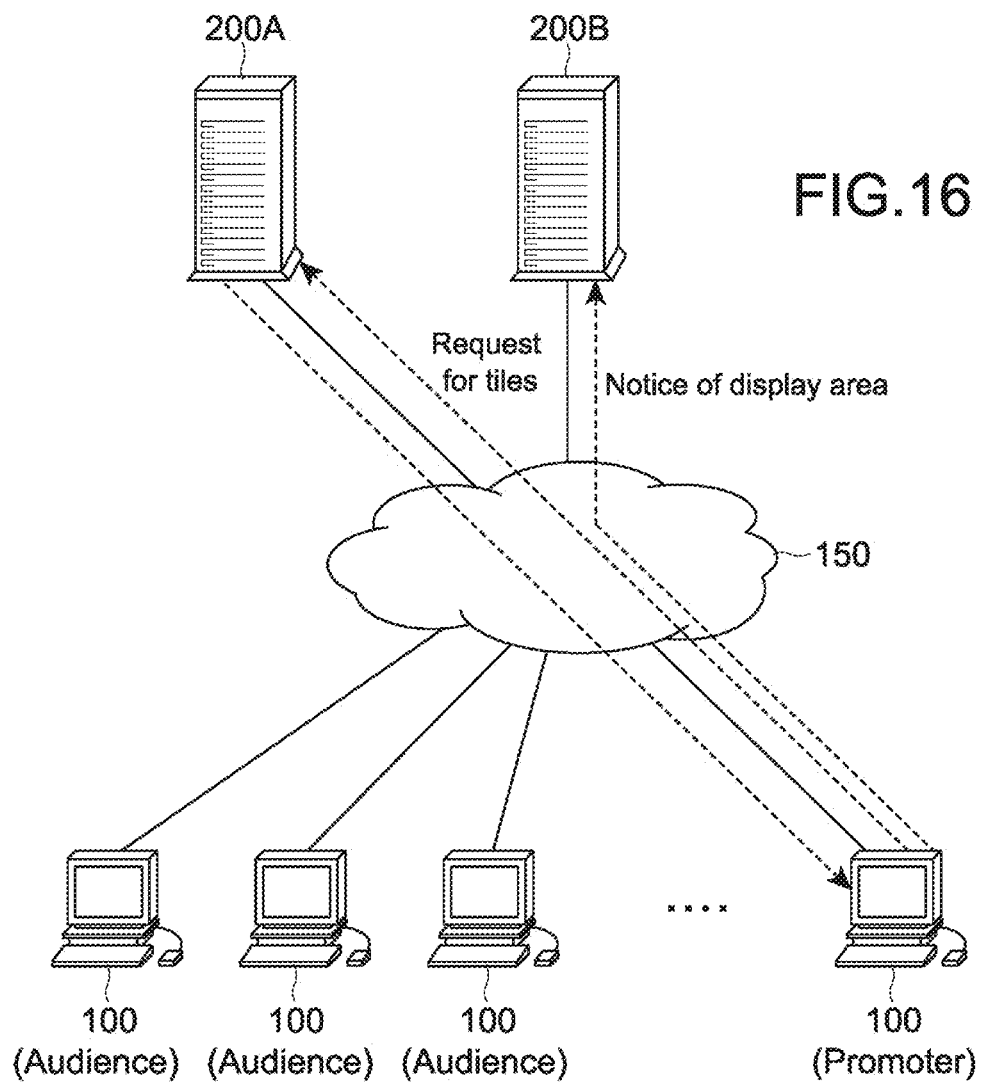
FIG. 16 is a block diagram showing the configuration of a teleconference system according to a third embodiment.

FIG. 16 is a block diagram showing the configuration of a teleconference system according to this embodiment.

In each of the embodiments described above, both the display area information and the tile data of the pathology image are stored in the server 200. However, it is not necessary to process both ones in the same server. Therefore, as shown in this figure, in this embodiment, a tile data server 200A for storing the tile data and a control data server 200B for processing the display area information are separately located. Further, in the control data server 200B, the past diagnosis record information described in the second embodiment, the list of tile data, the list of participants, and the like are managed (hereinafter, these data are called control data in a lump).

Therefore, the server is optimized for control data which has a small data capacity but needs a rapid response, and tile data which has a large data capacity and needs a high throughput.

Further, when the server 200B treating the control data does not exist, the control data may be exchanged in the P2P communication among a plurality of PC 100.

Fourth Embodiment

Next, a fourth embodiment according to the present technology will be described.

Figure 17:
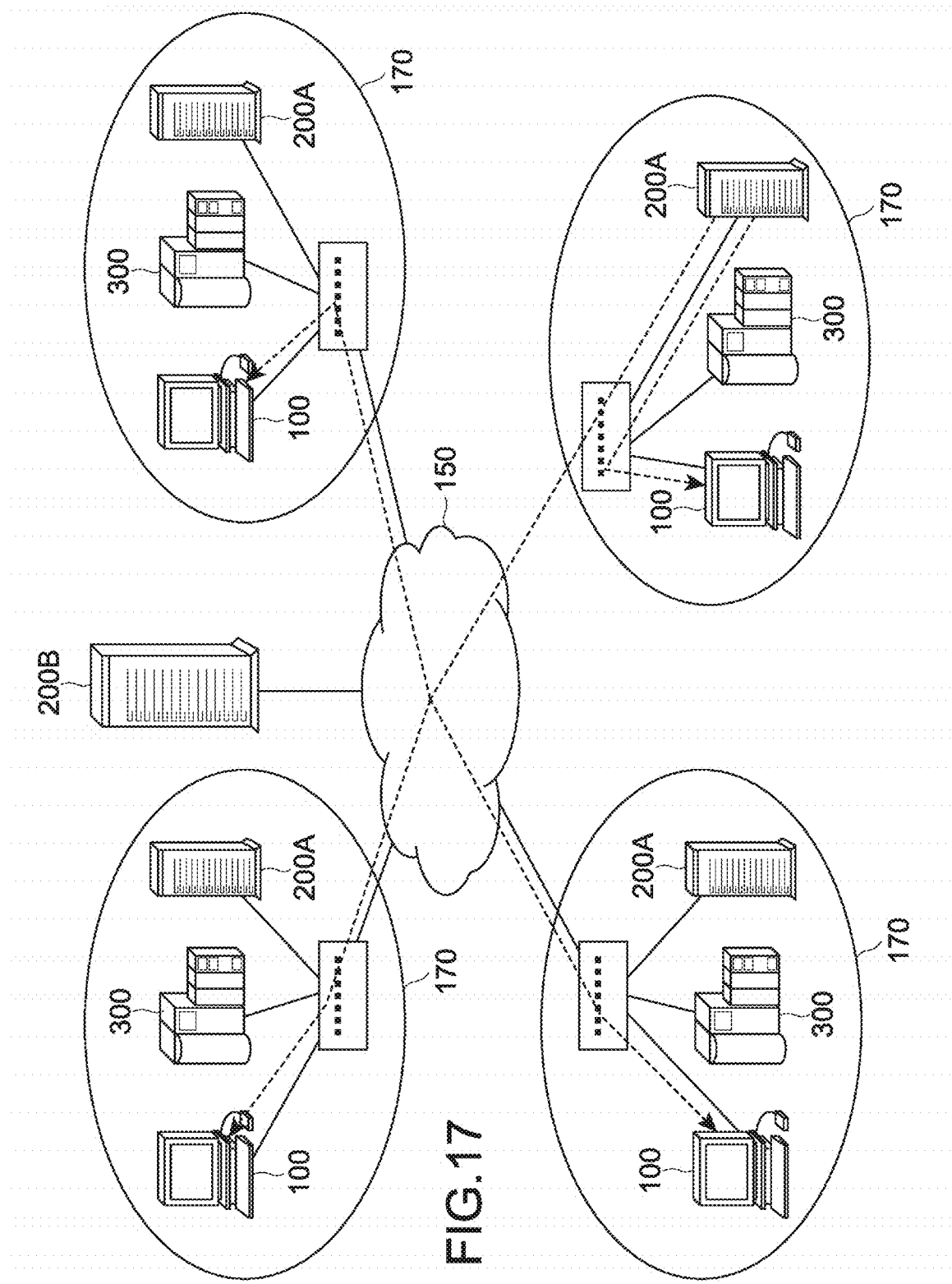
FIG. 17 is a block diagram showing the configuration of a teleconference system according to a fourth embodiment.

FIG. 17 is a block diagram showing the configuration of a teleconference system according to this embodiment.

As shown in this figure, a teleconference is held among a plurality of hospitals by connecting in-hospital networks 170 with one another. When pathology image data to be used in the conference are gathered to a single point, the cost for uploading and downloading is increased.

In contrast, pathology image data to be used in the teleconference are originally obtained by taking an image by a scanner 300 of each hospital and are retained in the in-hospital servers 200A. Therefore, as shown in this figure, in this embodiment, the in-hospital server 200A of each hospital is used in place of the tile data server 200A in the third embodiment. In this case, the control data server 200B also exists on the Internet 150.

Because of this configuration, the upload of the tile data to the server on the Internet 150 becomes unnecessary.

Fifth Embodiment

Next, a fifth embodiment according to the present technology will be described.

Figure 18:
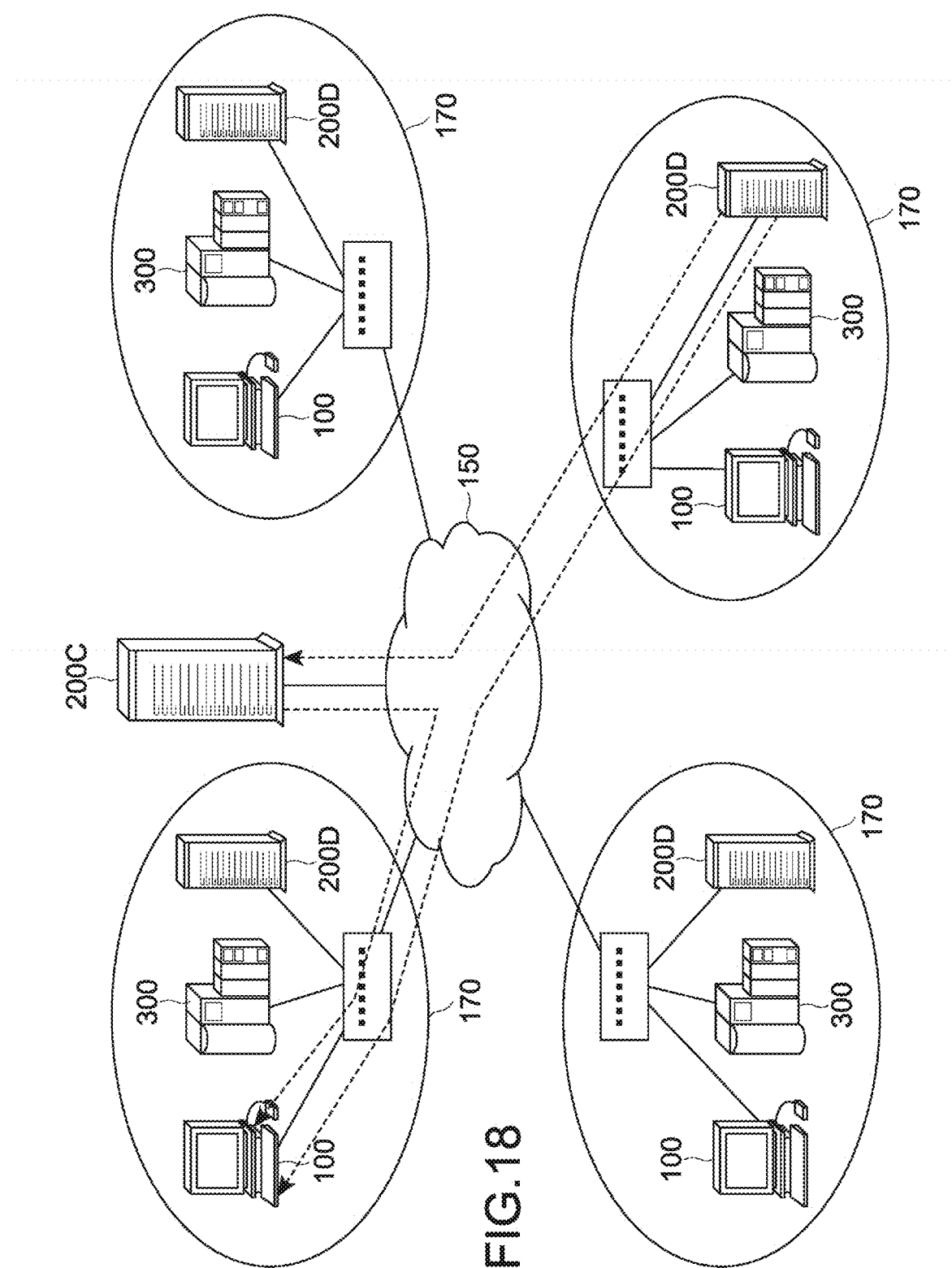
FIG. 18 is a block diagram showing the configuration of a teleconference system according to a fifth embodiment.

FIG. 18 is a block diagram showing the configuration of a teleconference system according to this embodiment.

In the fourth embodiment, it is substantially required that the in-hospital server delivers the tile data to participants of a teleconference. Therefore, there is a probability that a problem occurs in view of the load on the server depending on the network bandwidth and the number of the PCs 100.

Therefore, in this embodiment, as shown in this figure, tile data to be downloaded are uploaded to a cloud server 200C in advance. Accordingly, the load on the in-hospital server 200D is reduced.

Figure 19:
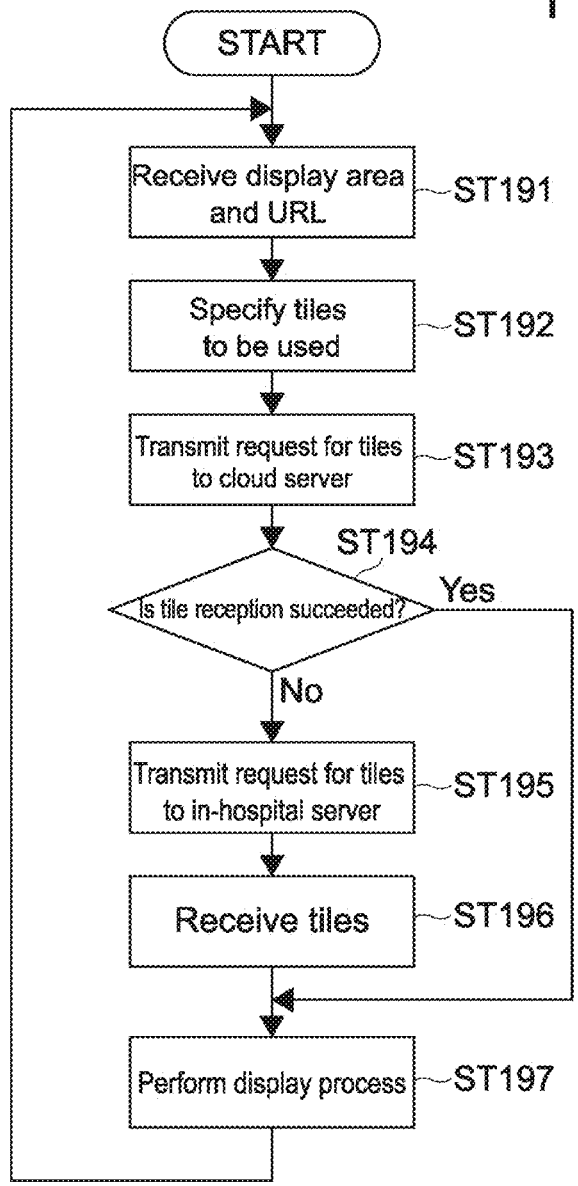
FIG. 19 is a flowchart showing the processing in a PC according to the fifth embodiment.

FIG. 19 is a flowchart showing the display process in the PC 100 according to this embodiment.

As shown in this figure, in the same manner as the processing in FIG. 6 and FIG. 15, when specifying tiles to be used (steps 191 and 192), the CPU 11 of the PC 100 transmits a request for the specified tiles to the cloud server 200C (step 193).

Then, the CPU 11 determines whether or not the tiles to be requested are successfully received (step 194).

When failing in the reception of the tiles (NO), the CPU 11 transmits a request for the tiles to the in-hospital server 200D (step 196), and receives the tiles (step 197). Thereafter, the received tiles are displayed (step 197).

Because of this processing, the working volume of the uploading of the tile data to the server 200C is suppressed, and the load on the in-hospital server 200D is also reduced.

Sixth Embodiment

Next, a sixth embodiment according to the present technology will be described.

FIG. 20 is a block diagram showing the configuration of a teleconference system according to this embodiment.

In each of the embodiments described above, there is only the single tile server. However, as shown in this figure, in this embodiment, a plurality of tile servers for delivering the same tile data are located (tile servers 200A-1 and 200A-2). For example, the tile server 200A-1 is set as a primary server, and the tile server 200A-2 is set as a secondary server.

Therefore, because a server optimum to one PC 100 being a client is determined for each PC 100, the system may cope with the increase in the number of PCs 100. In this case, each of the following server determining algorithms may be used.

A server is statistically allocated to one client in advance for each client.

The client (the PC 100) selects the server having the smallest RTT (Round Trip Time).

The client (the PC 100) selects the server having the widest bandwidth.

The primary server (the tile server 200A-1) determines while considering the total load.

The roundrobin processing is performed.

The load information of the server is periodically (e.g., every 10 seconds) obtained.

Seventh Embodiment

Next, a seventh embodiment according to the present technology will be described.

FIG. 21 is a block diagram showing the configuration of a teleconference system according to this embodiment.

As shown in this figure, in an in-hospital system in an in-hospital network 170, tile data for which a diagnosis was finished is retreated from the in-hospital network 170 to the cloud server 200C via the Internet 150.

Then, when the reservation of an in-hospital conference is performed in the in-hospital system while using the retreated data, the tile data retreated to the cloud server 200C is returned to the in-hospital server 200D at the time of the reservation.

[Modifications]

The present technology is not limited to only the embodiments described above, and may be variously modified within the scope not departing from the subject matter of this disclosure.

The configurations of the first to seventh embodiments may be combined with one another in any manner if the combined embodiments are not contradictory to one another. For example, the download process in advance in the second embodiment may be embodied in the configuration that the server is separately divided into the tile data server and the control data server as described in the third embodiment.

[Others]

In the present technology, the following configurations may be adopted.

In an embodiment, an information processing apparatus includes a processor and a memory device storing instructions. When executed by the processor, the instructions cause the processor to: (a) receive, from a first information processing apparatus, area specifying information and location information, the area specifying information specifying a display area in an image, the display area including a plurality of partial images, the location information indicating at least one location of the plurality of partial images; and (b) transmit, to a second information processing apparatus, the area specifying information and the location information.

In the information processing apparatus according to an embodiment, the image includes data representative of a slice of a biological tissue.

In the information processing apparatus according to an embodiment, (a) the information processing apparatus includes a server, (b) the first information processing apparatus includes a first personal computer; and (c) the second information processing apparatus includes a second personal computer.

In the information processing apparatus according to an embodiment, the plurality of partial images includes (a) a first partial image stored at a first location, and (b) a second partial image stored at a second location.

In the information processing apparatus according to an embodiment, the area specifying information is determined based on a display record.

In the information processing apparatus according to an embodiment, the area specifying information is determined based on annotation information.

In another embodiment, an information processing apparatus includes a processor, a display device, and a memory device storing instructions. When executed by the processor, the instructions cause the processor to: (a) in response to an operation input, determine area specifying information and location information, the area specifying information specifying a display area in an image, the display area including a plurality of partial images, the location information indicating at least one location of the plurality of partial images, (b) transmit the area specifying information and the location information to a first information processing apparatus, the first information processing apparatus being configured to, in response to receiving the area specifying information and the location information, transmit the area specifying information and the location information to a second information processing apparatus, (c) transmit a request for the plurality of partial images to the at least one location indicated by the location information, (d) receive the plurality of partial images from the at least one location; and (e) display the received plurality of partial images.

In the information processing apparatus according to an embodiment, the image includes data representative of a slice of a biological tissue.

In the information processing apparatus according to an embodiment, (a) the information processing apparatus includes a first personal computer, (b) the first information processing apparatus includes a server; and (c) the second information processing apparatus includes a second personal computer.

In the information processing apparatus according to an embodiment, the plurality of partial images includes: (a) a first partial image stored at a first location, and (b) a second partial image stored at a second location.

In the information processing apparatus according to an embodiment, the instructions, when executed by the processor, cause the processor to: (a) receive the first partial image from the first location, and (b) receive the second partial image from the second location.

In the information processing apparatus according to an embodiment, the instructions, when executed by the processor, cause the processor to: (a) determine whether the first partial image is stored by the memory device, (b) in response to a determination that the first partial image is stored by the memory device, read out the first partial image from the memory device, and (c) for the first partial image, do not transmit a request to the at least one location indicated by the location information.

In the information processing apparatus according to an embodiment, the instructions, when executed by the processor, cause the processor to determine the area specifying information based on a display record.

In the information processing apparatus according to an embodiment, the instructions, when executed by the processor, cause the processor to determine the area specifying information based on annotation information.

In another embodiment, an information processing apparatus includes a processor, a display device, and a memory device storing instructions. When executed by the processor, the instructions cause the processor to: (a) receive area specifying information and location information from a first information processing apparatus, the area specifying information specifying a display area in an image, the display area including a plurality of partial images, the location information indicating at least one location of the plurality of partial images, (b) transmit a request for the plurality of partial images to the at least one location indicated by the location information, (c) receive the plurality of partial images from the at least one location, and (d) display the received plurality of partial images.

In the information processing apparatus according to an embodiment, the image includes data representative of a slice of a biological tissue.

In the information processing apparatus according to an embodiment, (a) the information processing apparatus includes a personal computer, and (b) the first information processing apparatus includes a server.

In the information processing apparatus according to an embodiment, the plurality of partial images includes: (a) a first partial image stored at a first location, and (b) a second partial image stored at a second location.

In the information processing apparatus according to an embodiment, the instructions, when executed by the processor, cause the processor to: (a) receive the first partial image from the first location, and (b) receive the second partial image from the second location.

In the information processing apparatus according to an embodiment, the instructions, when executed by the processor, cause the processor to: (a) determine whether the first partial image is stored by the memory device, (b) in response to a determination that the first partial image is stored by the memory device, read out the first partial image from the memory device, and (c) for the first partial image, do not transmit a request to the at least one location indicated by the location information.

In the information processing apparatus according to an embodiment, the area specifying information is determined based on a display record.

In the information processing apparatus according to an embodiment, the area specifying information is determined based on annotation information.

In another embodiment, a method of operating an information processing apparatus includes (a) causing a processor to execute instructions to receive, from a first information processing apparatus, area specifying information and location information, the area specifying information specifying a display area in an image, the display area including a plurality of partial images, the location information indicating at least one location of the plurality of partial images, and (b) causing the processor to execute instructions to transmit, to a second information processing apparatus, the area specifying information and the location information.

In the method of operating an information processing apparatus according to an embodiment, the image includes data representative of a slice of a biological tissue.

In the method of operating an information processing apparatus according to an embodiment, (a) the information processing apparatus includes a server, (b) the first information processing apparatus includes a first personal computer, and (c) the second information processing apparatus includes a second personal computer.

In the method of operating an information processing apparatus according to an embodiment, the plurality of partial images includes: (a) a first partial image stored at a first location, and (b) a second partial image stored at a second location.

In the method of operating an information processing apparatus according to an embodiment, the area specifying information is determined based on a display record.

In the method of operating an information processing apparatus according to an embodiment, the area specifying information is determined based on annotation information.

In another embodiment, a system includes first, second, and third information processing apparatus. The first information processing apparatus is configured to, in response to an operation input, determine area specifying information and location information, the area specifying information specifying a display area in an image, the display area including a plurality of partial images, the location information indicating at least one location of the plurality of partial images. The second information processing apparatus is configured to receive the area specifying information and the location information from the first information processing apparatus. The third information processing apparatus is configured to: (a) receive the area specifying information and the location information from the second information processing apparatus, (b) transmit a request for the plurality of partial images to the at least one location indicated by the location information, (c) receive the plurality of partial images from the at least one location, and (d) display the received plurality of partial images.

The present application contains subject matter related to that disclosed in Japanese Priority Patent Application JP 2011-180438 filed in the Japan Patent Office on Aug. 22, 2011, the entire content of which is hereby incorporated by reference.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

REFERENCE SIGNS LIST

11 CPU
16 display
18 storage
19 communicating section
40 observation object
70 tile
71 coordinates moving path
72 display area
73 annotation
100 PC
150 Internet
170 in-hospital network
200 server
300 scanner

The invention claimed is:

1. An information processing apparatus used for information sharing, the information processing apparatus comprising:
   a processor; and
   a memory device storing instructions which when executed by the processor, cause the processor to:
   (a) receive, from a first information processing apparatus, area specifying information and location information, the area specifying information specifying a display area in an image, the display area including a plurality of partial images used at a high probability, the plurality of partial images being downloaded before the information sharing and stored in a plurality of different information processing apparatuses and the location information indicating at least one location of the plurality of partial images, wherein the plurality of partial images used at a high probability include a display operation record indicating at which magnification the plurality of partial images were viewed before the information sharing and how the display area was moved; and
   (b) transmit, to a second information processing apparatus, the area specifying information and the location information.

2. The information processing apparatus of claim 1, wherein the image includes data representative of a slice of a biological tissue.

3. The information processing apparatus of claim 1, wherein:
   (a) the information processing apparatus includes a server;
   (b) the first information processing apparatus includes a first user computer; and
   (c) the second information processing apparatus includes a second user computer.

4. The information processing apparatus of claim 1, wherein the area specifying information is determined based on a display record.

5. The information processing apparatus of claim 1, wherein the area specifying information is determined based on annotation information.

6. The information processing apparatus of claim 1, wherein the second information processing apparatus is configured to determine whether the area specifying information and the location information need to be updated.

7. The information processing apparatus of claim 1, wherein the plurality of different information processing apparatuses comprise the first information processing apparatus and the second information processing apparatus.

8. The information processing apparatus of claim 1, wherein the plurality of different information processing apparatuses comprise a server, a chairman computer, and an audience computer.

9. An information processing apparatus used for information sharing, the information processing apparatus comprising a first user computer, the first user computer comprising:
   a processor; a display device; and
   a memory device storing instructions which when executed by the processor, cause the processor to:
   (a) in response to an operation input, determine area specifying information and location information, the area specifying information specifying a display area in an image, the display area including a plurality of partial images used at a high probability, the plurality of partial images being downloaded before the information sharing and stored in a plurality of different information processing apparatuses, and the location information indicating at least one location of the plurality of partial images, wherein the plurality of partial images used at a high probability include a display operation record indicating at which magnification the plurality of partial images were viewed before the information sharing and how the display area was moved;
   (b) transmit the area specifying information and the location information to a first information processing apparatus, the first information processing apparatus being configured to, in response to receiving the area specifying information and the location information, transmit the area specifying information and the location information to a second information processing apparatus;
   (c) transmit a request for the plurality of partial images to the at least one location indicated by the location information;
   (d) receive the plurality of partial images from the at least one location; and
   (e) display the received plurality of partial images,
   the first information processing apparatus being a server and the second information processing apparatus being a second user computer.

10. The information processing apparatus of claim 9, wherein the image includes data representative of a slice of a biological tissue.

11. The information processing apparatus of claim 9, wherein the plurality of partial images includes:
   (a) a first partial image stored at a first location; and
   (b) a second partial image stored at a second location.

12. The information processing apparatus of claim 11, wherein the instructions, when executed by the processor, cause the processor to:

(a) receive the first partial image from the first location; and
(b) receive the second partial image from the second location.

13. The information processing apparatus of claim 11, wherein the instructions, when executed by the processor, cause the processor to:
   (a) determine whether the first partial image is stored by the memory device;
   (b) in response to a determination that the first partial image is stored by the memory device, read out the first partial image from the memory device; and
   (c) for the first partial image, do not transmit a request to the at least one location indicated by the location information.

14. The information processing apparatus of claim 11, wherein the first location and the second location are in the plurality of different information processing apparatuses.

15. The information processing apparatus of claim 9, wherein the instructions, when executed by the processor, cause the processor to determine the area specifying information based on a display record.

16. The information processing apparatus of claim 9, wherein the instructions, when executed by the processor, cause the processor to determine the area specifying information based on annotation information.

17. An information processing apparatus used for information sharing, the information processing apparatus comprising:
   a processor;
   a display device; and
   a memory device storing instructions which when executed by the processor, cause the processor to:
   (a) receive area specifying information and location information from a first information processing apparatus, the area specifying information specifying a display area in an image, the display area including a plurality of partial images used at a high probability, the plurality of partial images being downloaded before the information sharing and stored in a plurality of different information processing apparatuses and the location information indicating at least one location of the plurality of partial images, wherein the plurality of partial images used at a high probability include a display operation record indicating at which magnification the plurality of partial images were viewed before the information sharing and how the display area was moved;
   (b) transmit a request for the plurality of partial images to the at least one location indicated by the location information;
   (c) receive the plurality of partial images from the at least one location; and
   (d) display the received plurality of partial images.

18. The information processing apparatus of claim 17, wherein the image includes data representative of a slice of a biological tissue.

19. The information processing apparatus of claim 17, wherein:
   (a) the information processing apparatus includes a user computer; and
   (b) the first information processing apparatus includes a server.

20. The information processing apparatus of claim 17, wherein the instructions, when executed by the processor, cause the processor to:
   (a) receive a first partial image from one of the plurality of different information processing apparatuses; and
   (b) receive a second partial image from another of the plurality of different information processing apparatuses.

21. The information processing apparatus of claim 17, wherein the instructions, when executed by the processor, cause the processor to:
   (a) determine whether a first partial image is stored by the memory device;
   (b) in response to a determination that the first partial image is stored by the memory device, read out the first partial image from the memory device; and
   (c) for the first partial image, do not transmit a request to the at least one location indicated by the location information.

22. The information processing apparatus of claim 17, wherein the area specifying information is determined based on a display record.

23. The information processing apparatus of claim 17, wherein the area specifying information is determined based on annotation information.

24. The information processing apparatus of claim 17, wherein the plurality of different information processing apparatuses comprise the first information processing apparatus and a second information processing apparatus.

25. A method of operating an information processing apparatus used for information sharing, the method comprising:
   (a) causing a processor to execute instructions to receive, from a first information processing apparatus, area specifying information and location information, the area specifying information specifying a display area in an image, the display area including a plurality of partial images used at a high probability, the plurality of partial images being downloaded before the information sharing and stored in a plurality of different information processing apparatuses and the location information indicating at least one location of the plurality of partial images, wherein the plurality of partial images used at a high probability include a display operation record indicating at which magnification the plurality of partial images were viewed before the information sharing and how the display area was moved; and
   (b) causing the processor to execute instructions to transmit, to a second information processing apparatus, the area specifying information and the location information.

26. The method of claim 25, wherein the image includes data representative of a slice of a biological tissue.

27. The method of claim 25, wherein:
   (a) the information processing apparatus includes a server;
   (b) the first information processing apparatus includes a first user computer; and
   (c) the second information processing apparatus includes a second user computer.

28. The method of claim 25, wherein the area specifying information is determined based on a display record.

29. The method of claim 25, wherein the area specifying information is determined based on annotation information.

30. The method of claim 25, wherein the plurality of different information processing apparatuses comprise the first information processing apparatus and the second information processing apparatus.

31. A system used for information sharing, the system comprising:
   a first information processing apparatus configured to, in response to an operation input, determine area specifying information and location information, the area specifying information specifying a display area in an image, the display area including a plurality of partial images used at a high probability, the plurality of partial images being downloaded before the information sharing and stored in a plurality of different information processing apparatuses and the location information indicating at least one location of the plurality of partial images, wherein the plurality of partial images used at a high probability include a display operation record indicating at which magnification the plurality of partial images were viewed before the information sharing and how the display area was moved;

a second information processing apparatus configured to receive the area specifying information and the location information from the first information processing apparatus, a third information processing apparatus configured to:

(a) receive the area specifying information and the location information from the second information processing apparatus;

(b) transmit a request for the plurality of partial images to the at least one location indicated by the location information;

(c) receive the plurality of partial images from the at least one location; and (d) display the received plurality of partial images.

32. The system of claim 31, wherein the plurality of different information processing apparatuses comprise the first information processing apparatus and the second information processing apparatus.

* * * * *